(12) United States Patent
Watanabe et al.

(10) Patent No.: US 10,875,008 B2
(45) Date of Patent: *Dec. 29, 2020

(54) SEPARATION MATERIAL

(71) Applicant: Hitachi Chemical Company, LTD., Tokyo (JP)

(72) Inventors: Masaru Watanabe, Tokyo (JP); Tomoko Higashiuchi, Tokyo (JP); Fumihiko Kawauchi, Tokyo (JP); Yasushi Gotoh, Tokyo (JP); Michio Butsugan, Hitachi (JP); Ryoichi Nakanishi, Tokyo (JP)

(73) Assignee: SHOWA DENKO MATERIALS CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/544,369

(22) PCT Filed: Jan. 19, 2016

(86) PCT No.: PCT/JP2016/051476
§ 371 (c)(1),
(2) Date: Jul. 18, 2017

(87) PCT Pub. No.: WO2016/117574
PCT Pub. Date: Jul. 28, 2016

(65) Prior Publication Data

US 2017/0368533 A1    Dec. 28, 2017

(30) Foreign Application Priority Data

Jan. 19, 2015  (JP) ................ 2015-007775
Jan. 15, 2016  (JP) ................ 2016-006241
Jan. 15, 2016  (JP) ................ 2016-006242

(51) Int. Cl.
*B01J 20/26*  (2006.01)
*G01N 30/88*  (2006.01)
(Continued)

(52) U.S. Cl.
CPC .......... *B01J 20/267* (2013.01); *B01D 15/206* (2013.01); *B01D 15/361* (2013.01); *B01J 20/24* (2013.01);
(Continued)

(58) Field of Classification Search
None
See application file for complete search history.

(56) References Cited

U.S. PATENT DOCUMENTS 3,966,489 A    6/1976   Barrett et al.
4,335,017 A    6/1982   Miles et al.
(Continued)

FOREIGN PATENT DOCUMENTS

EP    2545989 A1   1/2013
JP    S60-169427 A  9/1985
(Continued)

OTHER PUBLICATIONS

Zhou, W. Q.; Gu, T. Y.; Su, Z. G.; Ma, G. H. Polymer 2007, 48, 1981-1988.*
(Continued)

*Primary Examiner* — Krishnan S Menon
(74) *Attorney, Agent, or Firm* — Fitch, Even, Tabin & Flannery, LLP

(57) ABSTRACT

The present invention provides a separation material that comprises porous polymer particles comprising a styrene-based monomer as a monomer unit; and a coating layer comprising a macromolecule having hydroxyl groups, which covers at least a portion of the surface of the porous polymer particles, and the separation material has a 5%
(Continued)

compressive deformation modulus of 100 to 1,000 MPa, and has a mode diameter in the pore size distribution of 0.1 to 0.5 µm.

18 Claims, 1 Drawing Sheet

(51) Int. Cl.
| | |
|---|---|
| *B01J 20/28* | (2006.01) |
| *B01J 20/24* | (2006.01) |
| *B01D 15/20* | (2006.01) |
| *B01D 15/36* | (2006.01) |
| *B01J 20/32* | (2006.01) |
| *C07K 1/18* | (2006.01) |
| *C07K 1/16* | (2006.01) |
| *B01J 20/281* | (2006.01) |
| *G01N 30/60* | (2006.01) |
| *G01N 30/02* | (2006.01) |

(52) U.S. Cl.
CPC ............ *B01J 20/261* (2013.01); *B01J 20/28* (2013.01); *B01J 20/28011* (2013.01); *B01J 20/28088* (2013.01); *B01J 20/321* (2013.01); *B01J 20/327* (2013.01); *C07K 1/18* (2013.01); *G01N 30/88* (2013.01); *B01J 2220/54* (2013.01); *B01J 2220/58* (2013.01); *C07K 1/16* (2013.01); *G01N 30/482* (2013.01); *G01N 30/60* (2013.01); *G01N 2030/027* (2013.01)

(56) References Cited

U.S. PATENT DOCUMENTS

| | | | |
|---|---|---|---|
| 4,336,161 | A | 6/1982 | Rosevear et al. |
| 4,965,289 | A | 10/1990 | Sherrington et al. |
| 5,114,577 | A | 5/1992 | Kusano et al. |
| 6,572,766 | B1 * | 6/2003 | Bergstrom ............ B01J 20/285 210/198.2 |
| 2003/0129296 | A1 * | 7/2003 | Kelso ................... B01J 19/0046 506/9 |
| 2003/0150813 | A1 | 8/2003 | Hayashi et al. |
| 2005/0191426 | A1 * | 9/2005 | Moya .................... B01J 20/3282 427/372.2 |
| 2005/0211615 | A1 * | 9/2005 | DiLeo .................. B01J 20/3293 210/198.2 |
| 2007/0069408 | A1 * | 3/2007 | Cheng .................. B01J 20/3282 264/4.1 |
| 2007/0248957 | A1 * | 10/2007 | Nova .................... B01J 19/0046 435/6.12 |
| 2013/0225701 | A1 * | 8/2013 | Soice .................. B01J 20/28092 521/31 |

FOREIGN PATENT DOCUMENTS

| | | |
|---|---|---|
| JP | S63-236539 A | 10/1988 |
| JP | H1-254247 A | 9/1998 |
| JP | 2003-093801 A | 4/2003 |
| JP | 2006-095516 A | 4/2006 |
| JP | 2007-017445 A | 1/2007 |
| JP | 2009-221428 A | 10/2009 |
| JP | 2009-244067 A | 10/2009 |
| JP | 2014-521078 A | 8/2014 |
| WO | 2006/025556 A1 | 3/2006 |

OTHER PUBLICATIONS

International Preliminary Report on Patentability of Appln. No. PCT/JP2016/051476 dated Aug. 3, 2017 in English.
International Search Report for PCT/JP2016/051476 dated Mar. 22, 2016; English translation submitted herewith (7 pages).
Qu Jian-Bo et al, "A novel stationary phase derivatized from hydrophilic gigaporous polystyrene-based microspberes for high-speed protein chromatography", Journal of Chromatography A, 2009, 1216, p. 6511-p. 6516.
Qu Jian-Bo et al, "An Effective Way to Hydrophilize Gigaporous Polystyrene Microspheres as Rapid Chromatographic Separation Media for Proteins", Langmuir, 2008, 24, p. I3646-p. I3652.

* cited by examiner

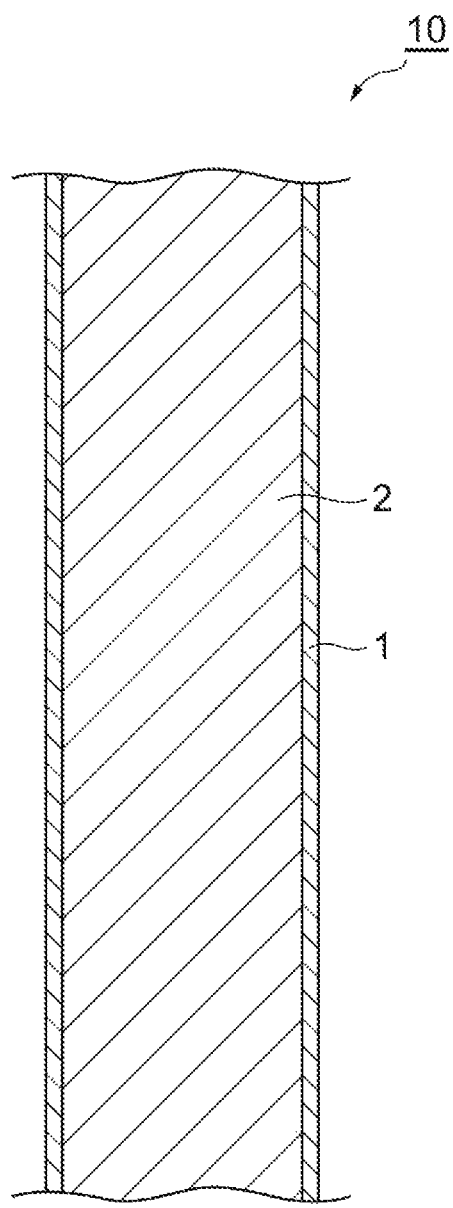

SEPARATION MATERIAL

CROSS-REFERENCE TO RELATED APPLICATIONS

This application is a U.S. national phase application filed under 35 U.S.C. § 371 of International Application PCT/JP2016/051476, filed on Jan. 19, 2016, designating the United States, which claims benefit of the filing dates of JP 2015-007775, filed Jan. 19, 2015, JP 2016-006241, filed Jan. 15, 2016, and JP 2016-006242, filed Jan. 15, 2016, each of which is hereby incorporated herein by reference in its entirety.

TECHNICAL FIELD

The present invention relates to a separation material.

BACKGROUND ART

Conventionally, in a case in which bio-macromolecules that are represented by proteins are separated and purified, generally, an ion exchanger having a porous type synthetic macromolecule as a matrix, an ion exchanger having a crosslinked gel of a hydrophilic natural macromolecule as a matrix, and the like are used. Since an ion exchanger having a porous type synthetic macromolecule as a matrix undergoes a small volume change caused by salt concentration, when the ion exchanger is packed into a column and used for chromatography, the ion exchanger tends to have excellent pressure resistance at the time of liquid permeation. However, when this ion exchanger is used for the separation of a protein or the like, non-specific adsorption such as irreversible adsorption based on hydrophobic interaction occurs, and therefore, there is a problem that asymmetrization of peaks occurs, or a protein adsorbed to an ion exchanger by the hydrophobic interaction remains adsorbed and cannot be collected.

Meanwhile, in the case of ion exchangers having crosslinked gels of hydrophilic natural macromolecule, which are represented by polysaccharides such as dextran and agarose as matrices, there is an advantage that non-specific adsorption of proteins hardly occurs. However, these ion exchangers have a defect that the ion exchangers swell conspicuously in aqueous solutions, undergo a large volume change due to the ionic strength of a solution and a large volume change between free acid type and load-sensitive type, and do not have sufficient mechanical strength. Particularly, in the case of using a crosslinked gel in chromatography, the ion exchangers have a defect that there is a high pressure loss at the time of liquid permeation, and the gel is consolidated as a result of liquid permeation.

In order to overcome the defects of crosslinked gels of hydrophilic natural macromolecules, attempts have been hitherto made to mix the crosslinked gels with rigid substances that serve as a so-called "skeleton". For example, a composite in which a gel such as a natural macromolecule gel is retained within pores of a porous macromolecule is known in the field of peptide synthesis (see, for example, Patent Literature 1). By using such a composite, the load factor of a reactive substance is increased, and synthesis with high yield is enabled. Furthermore, since a hard synthetic macromolecule substance is surrounded by a gel, there is an advantage that even if the composite is used in the form of a column bed, there is no change in volume, and the pressure of the flow-through that permeates through the column does not change.

Separation materials, in which a xerogel of a polysaccharide such as dextran or cellulose is retained in an inorganic porous body such as celite, are known (see, for example, Patent Literature 2 and Patent Literature 3). This gel is provided with a diethylaminoethyl (DEAE) group or the like in order to add adsorption performance, and the gel is used for the removal of hemoglobin. These separation materials have satisfactory liquid permeability in columns.

An ion exchanger of a hybrid copolymer, in which pores of a copolymer having a macro network structure are filled with a crosslinked copolymer gel synthesized from monomers, is known (see, for example, Patent Literature 4). A crosslinked copolymer gel has problems with pressure loss, volume change and the like in the case of having a low degree of crosslinking; however, the liquid permeation characteristics are improved by employing a hybrid copolymer, thus the pressure loss is decreased, the ion exchange capacity is increased, and the leakage behavior is improved.

Compositized filler materials in which a crosslinked gel of a hydrophilic natural macromolecule having a macro network structure is filled in the pores of an organic synthetic polymer base, have been proposed (see, for example, Patent Literature 5 and Patent Literature 6).

Synthesis of porous particles formed by copolymerization of glycidyl methacrylate and an acrylic crosslinking monomer is known (see, for example, Patent Literature 7).

CITATION LIST

Patent Literature

Patent Literature 1: U.S. Pat. No. 4,965,289
Patent Literature 2: U.S. Pat. No. 4,335,017
Patent Literature 3: U.S. Pat. No. 4,336,161
Patent Literature 4: U.S. Pat. No. 3,966,489
Patent Literature 5: JP H01-254247 A
Patent Literature 6: U.S. Pat. No. 5,114,577
Patent Literature 7: JP 2009-244067 A

SUMMARY OF INVENTION

Technical Problem

However, conventional separation materials do not have both the characteristic of having excellent amount of protein adsorption, and the characteristic of having excellent column characteristics such as liquid permeability when used as columns, at sufficient levels.

The present invention was achieved in view of such circumstances, and it is an object of the invention to provide a separation material having an excellent amount of protein adsorption and having excellent column characteristics such as liquid permeability when used as a column.

Solution to Problem

The present invention provides a separation material or a separatory column described in the following [1] to [18].

[1] A separation material comprising porous polymer particles that comprise a styrene-based monomer as a monomer unit; and a coating layer that comprises a macromolecule having hydroxyl groups and covers at least a portion of the surface of the porous polymer particles, wherein the 5% compressive deformation modulus of the separation material is 100 to 1,000 MPa, and the mode in the pore size distribution is 0.1 to 0.5 μm.

[2] The separation material according to [1], wherein the degree of hygroscopicity is 1% to 30% by mass.

[3] A separation material comprising porous polymer particles; and a coating layer that covers at least a portion of the surface of the porous polymer particles, wherein the coating layer comprises a macromolecule having hydroxyl groups, the compressive deformation rate at the time when the separation material is compressed at 50 mN in a wet state is less than 30% of the particle size, and the ratio of the compression recovery rate in a wet state with respect to the compression recovery rate in a dry state at the time when the separation material is compressed at 50 mN is 0.8 or higher.

[4] A separation material comprising porous polymer particles; and a coating layer that covers at least a portion of the surface of the porous polymer particles, wherein the coating layer comprises a macromolecule having hydroxyl groups, the 5% compressive deformation modulus of the separation material in a wet state is 100 MPa or greater, and the ratio of the 5% compressive deformation modulus in a dry state with respect to the 5% compressive deformation modulus in a wet state of the separation material is 1.85 or higher.

[5] The separation material according to [3] or [4], wherein the mode diameter in the pore size distribution is 0.05 to 0.5 μm.

[6] The separation material according to any one of [1] to [5], wherein the average particle size of the porous polymer particles is 10 to 500 μm.

[7] The separation material according to any one of [1] to [6], wherein the coefficient of variation of the particle size of the porous polymer particles is 3% to 15%.

[8] The separation material according to any one of [1] to [7], wherein the average particle size of the separation material is 10 to 500 μm.

[9] The separation material according to any one of [1] to [8], wherein the pore volume of the separation material is 30% by volume or more.

[10] The separation material according to any one of [1] to [9], wherein the specific surface area of the porous polymer particles is 30 $m^2/g$ or more.

[11] The separation material according to any one of [1] to [10], wherein the specific surface area of the separation material is 30 $m^2/g$ or more.

[12] The separation material according to any one of [1] to [11], wherein the porous polymer particles comprise divinylbenzene as a monomer unit at a proportion of 50% by mass or more based on the total mass of the monomers.

[13] The separation material according to any one of [1] to [12], wherein the macromolecule having hydroxyl groups is a polysaccharide or a modification product thereof.

[14] The separation material according to any one of [1] to [12], wherein the macromolecule having hydroxyl groups is agarose or a modification product thereof.

[15] The separation material according to any one of [1] to [14], wherein the macromolecule having hydroxyl groups is crosslinked.

[16] The separation material according to any one of [1] to [15], wherein the separation material comprises 30 to 500 mg of the coating layer per 1 g of the porous polymer particles.

[17] The separation material according to any one of [1] to [16], wherein in the case of being packed in a column, when the column pressure is 0.3 MPa, the liquid permeation rate is 800 cm/h or higher.

[18] A separatory column comprising a column; and the separation material according to any one of [1] to [18] that is packed in the column.

Advantageous Effects of Invention

According to the present invention, a separation material that has an excellent protein adsorption amount and excellent column characteristics such as liquid permeability when used as a column, can be provided.

BRIEF DESCRIPTION OF DRAWINGS

FIG. 1 is a cross-sectional view illustrating an embodiment of a separatory column.

DESCRIPTION OF EMBODIMENTS

Hereinafter, suitable embodiments of the present invention will be described; however, the present invention is not intended to be limited to these embodiments.

First Embodiment

<Separation Material>

A separation material according to a first embodiment will be explained below. The separation material of the present embodiment comprises porous polymer particles; and a coating layer that covers at least a portion of the surface of the porous polymer particles. According to the present embodiment, a separation material that exhibits reduced non-specific adsorption of proteins, has excellent alkali resistance and durability, and has excellent column characteristics such as liquid permeability when used as a column, and a separatory column using this separation material can be provided. In the present embodiment, the "surface of the porous polymer particles" is meant to include not only the external surface of the porous polymer particles, but also the surface of pores in the interior of the porous polymer particles.

(Porous Polymer Particles)

The porous polymer particles of the present embodiment are particles obtained by curing a monomer including a porosifier, and can be synthesized by, for example, conventional suspension polymerization and emulsion polymerization. There are no particular limitations on the monomer, and for example, a styrene-based monomer can be used. Specific examples of the monomer include polyfunctional monomers and monofunctional monomers such as follows.

Examples of the polyfunctional monomers include divinyl compounds such as divinylbenzene, divinylbiphenyl, divinylnaphthalene, and divinylphenanthrene. These polyfunctional monomers can be used singly, or in combination of two or more kinds thereof. Among the above-described monomers, from the viewpoint of having excellent durability, acid resistance and alkali resistance, it is preferable to use divinylbenzene.

In a case in which the porous polymer particles comprise divinylbenzene as a monomer unit, it is preferable that the polymer particles comprise divinylbenzene at a proportion of 50% by mass or more, more preferably at a proportion of 60% by mass or more, and even more preferably at a proportion of 70% by mass or more, based on the total mass of the monomers. When the porous polymer particles comprise divinylbenzene at a proportion of 50% by mass or more based on the total mass of the monomers, the porous polymer particles tend to have excellent alkali resistance and pressure resistance.

Examples of the monofunctional monomers include styrene and derivatives thereof, such as styrene, o-methylstyrene, m-methylstyrene, p-methylstyrene, α-methylstyrene, o-ethylstyrene, m-ethylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, and 3,4-dichlorostyrene. These monofunctional monomers can be used singly or in combination of two or more kinds thereof. Among these, from the viewpoint of obtaining excellent acid resistance and alkali resistance, it is preferable to use styrene. Furthermore, styrene derivatives having functional groups such as a carboxyl group, an amino group, a hydroxyl group and an aldehyde group, can also be used.

Examples of the porosifier include aliphatic or aromatic hydrocarbons, esters, ketones, ethers, and alcohols, which are organic solvents that accelerate phase separation at the time of polymerization and accelerate porosification of particles. Specific examples include toluene, xylene, diethylbenzene, cyclohexane, octane, butyl acetate, dibutyl phthalate, methyl ethyl ketone, dibutyl ether, 1-hexanol, 2-octanol, decanol, lauryl alcohol, and cyclohexanol. These porosifiers can be used singly or in combination of two or more kinds thereof.

The porosifier can be used in an amount of 0% to 200% by mass with respect to the total mass of the monomers. Porosity of the porous polymer particles can be controlled by the amount of the porosifier. Furthermore, the size and shape of the pores of the porous polymer particles can be controlled by the type of the porosifier.

Water that is used as a solvent can also be used as the porosifier. In a case in which water is used as the porosifier, porosification can be achieved by dissolving an oil-soluble surfactant in the monomer, and absorbing water.

Examples of the oil-soluble surfactant that is used for porosification include a sorbitan monoester of a branched C16-C24 fatty acid, a linear unsaturated C16-C22 fatty acid or a linear saturated C12-C14 fatty acid, for example, sorbitan monolaurate, sorbitan monooleate, sorbitan monomyristate, or a sorbitan monoester derived from coconut fatty acids; a diglycerol monoester of a branched C16-C24 fatty acid, a linear unsaturated C16-C22 fatty acid, or a linear saturated C12-C14 fatty acid, for example, diglycerol monooleate (for example, a diglycerol monoester of a C18:1 (number of carbon atoms: 18, number of double bonds: 1) fatty acid), diglycerol monomyristate, diglycerol monoisostearate, or diglycerol monoester of coconut fatty acids; a diglycerol monoaliphatic ether of a branched C16-C24 alcohol (for example, Guerbet alcohol), a linear unsaturated C16-C22 alcohol, or a linear saturated C12-C14 alcohol (for example, coconut fatty alcohol); and mixtures of these.

Among these, sorbitan monolaurate (for example, SPAN (registered trademark) 20; sorbitan monolaurate preferably having a purity of higher than about 40%, more preferably a purity of higher than about 50%, and most preferably a purity of higher than about 70%); sorbitan monooleate (for example, SPAN (registered trademark) 80; sorbitan monooleate preferably having a purity of higher than about 40%, more preferably a purity of about 50%, and most preferably a purity of higher than about 70%); diglycerol monooleate (for example, diglycerol monooleate preferably having a purity of higher than about 40%, more preferably a purity of higher than about 50%, and most preferably a purity of higher than about 70%); diglycerol monoisostearate (for example, diglycerol monoisostearate preferably having a purity of higher than about 40%, more preferably a purity of higher than about 50%, and most preferably a purity of higher than about 70%); diglycerol monomyristate (sorbitan monomyristate preferably having a purity of higher than about 40%, more preferably a purity of higher than about 50%, and most preferably a purity of higher than about 70%); cocoyl (for example, a lauryl group or a myristoyl group) ether of diglycerol; and mixtures of these, are preferred.

It is preferable to use these oil-soluble surfactants in an amount in the range of 5% to 80% by mass with respect to the total mass of the monomers. When the content of the oil-soluble surfactant is 5% by mass or more, since stability of water droplets becomes sufficient, it is difficult for large single holes to be formed. Furthermore, when the content of the oil-soluble surfactant is 80% by mass or less, it is easier for the porous polymer particles to maintain the shape after polymerization.

Examples of an aqueous medium that is used for the polymerization reaction include water, and a mixed medium of water and a water-soluble solvent (for example, a lower alcohol). The aqueous medium may include a surfactant. As the surfactant, among anionic, cationic, nonionic and zwitterionic surfactants, all can be used.

Examples of anionic surfactants include fatty acid oils such as sodium oleate and castor oil potassium; alkyl sulfuric acid ester salts such as sodium lauryl sulfate and ammonium lauryl sulfate; alkyl benzenesulfonic acid salts such as sodium dodecyl benzenesulfonate; alkyl naphthalenesulfonic acid salts; alkane sulfonic acid salts; dialkyl sulfosuccinic acid salts such as sodium dioctyl sulfosuccinate; alkenyl succinic acid salts (dipotassium salts); alkyl phosphoric acid ester salts; naphthalenesulfonic acid-formalin condensate, polyoxyethylene alkyl phenyl ether sulfuric acid ester salts; polyoxyethylene alkyl ether sulfuric acid salts such as sodium polyoxyethylene lauryl ether sulfate; and polyoxyethylene alkyl sulfuric acid ester salts.

Examples of cationic surfactants include alkyl amine salts such as lauryl amine acetate and stearyl amine acetate; and quaternary ammonium salts such as lauryl trimethylammonium chloride.

Examples of nonionic surfactants include hydrocarbon-based nonionic surfactants such as polyethylene glycol alkyl ethers, polyethylene glycol alkyl aryl ethers, polyethylene glycol esters, polyethylene glycol sorbitan esters, and polyalkylene glycol alkyl amines or amides; polyether-modified silicone-based nonionic surfactants such as polyethylene oxide adducts and polypropylene oxide adducts of silicones; and fluorine-based nonionic surfactants such as perfluoroalkyl glycols.

Examples of zwitterionic surfactants include hydrocarbon surfactants such as lauryl dimethylamine oxide; phosphoric acid ester-based surfactants, and phosphorous acid ester-based surfactants.

The surfactants may be used singly or in combination of two or more kinds thereof. Among the surfactants described above, from the viewpoint of dispersion stability at the time of polymerizing the monomers, anionic surfactants are preferred.

As a polymerization initiator that is added as necessary, for example, organic peroxides such as benzoyl peroxide, lauroyl peroxide, benzoyl orthochloroperoxide, benzoyl orthomethoxyperoxide, 3,5,5-trimethylhexanoyl peroxide, tert-butyl peroxy-2-ethylhexanoate, and di-tert-butyl peroxide; azo-based compounds such as 2,2'-azobisisobutyronitrile, 1,1'-azobiscyclohexanecarbonitrile, and 2,2'-azobis(2,4-dimethylvaleronitrile). The polymerization initiator can be used in an amount in the range of 0.1 to 7.0 parts by mass with respect to 100 parts by mass of the monomers.

The polymerization temperature can be appropriately selected according to the types of the monomer and the polymerization initiator. The polymerization temperature is preferably 25° to 110° C., and more preferably 50° C. to 100° C.

In regard to the synthesis of porous polymer particles, in order to enhance dispersion stability of the particles, a macromolecule dispersion stabilizer may also be used.

Examples of the macromolecule dispersion stabilizer include polyvinyl alcohol, polycarboxylic acids, celluloses (hydroxyethyl cellulose, carboxymethyl cellulose, methyl cellulose, and the like), and polyvinylpyrrolidone, and inorganic water-soluble macromolecule compounds such as sodium tripolyphosphate can also be used in combination. Among these, polyvinyl alcohol or polyvinylpyrrolidone is preferred. The amount of addition of the macromolecule dispersion stabilizer is preferably 1 to 10 parts by mass with respect to 100 parts by mass of the monomers.

In order to prevent the monomers from being polymerized alone, water-soluble polymerization inhibitors such as nitrous acid salts, sulfurous acid salts, hydroquinones, ascorbic acids, water-soluble vitamins B compounds, citric acid, and polyphenols may also be used.

The average particle size of the porous polymer particles is preferably 500 μm or less, more preferably 300 μm or less, even more preferably 150 μm or less, and still more preferably 100 μm or less. Furthermore, the average particle size of the porous polymer particles is preferably 10 μm or more, more preferably 30 μm or more, and even more preferably 50 μm or more, from the viewpoint of enhancing liquid permeability.

The coefficient of variation (C.V.) of the particle size of the porous polymer particles is preferably 3% to 15%, more preferably 5% to 15%, and even more preferably 5% to 10%, from the viewpoint of enhancing liquid permeability. As a method for reducing the C.V., a method of monodispersing the porous polymer particles by means of an emulsifying apparatus such as a MICRO PROCESS SERVER (manufactured by Hitachi, Ltd.) may be used.

The average particle size and the C.V. (coefficient of variation) of the particle size of the porous polymer particles or the separation material can be determined by the following measurement method.

1) Particles are dispersed in water (including a dispersant such as a surfactant) using an ultrasonic dispersing apparatus, and thus a dispersion liquid including 1% by mass of porous polymer particles is prepared.

2) The average particle size and the C.V. (coefficient of variation) of the particle size are measured from the images of about 10,000 particles in the dispersion liquid, using a particle size distribution meter (SYSMEX FLOW, manufactured by Sysmex Corp.).

The pore volume (porosity) of the porous polymer particles is preferably from 30% to 70% by volume, and more preferably from 40% to 70% by volume, based on the total volume (including the pore volume) of the porous polymer particles. It is preferable that the porous polymer particles have pores having a pore size of 0.1 μm or more and less than 0.5 μm, that is, macropores (macrovoids). The mode diameter in the pore size distribution (most frequent value of the pore size distribution, maximum frequency pore size, average pore size) of the porous polymer particles is preferably 0.1 μm or more and less than 0.5 μm, and more preferably 0.2 μm or more and less than 0.5 μm. When the mode diameter in the pore size distribution is 0.1 μm or more, there is a tendency that substances can easily enter into the pores, and when the mode diameter in the pore size distribution is less than 0.5 μm, the specific surface area becomes sufficient. These can be adjusted by means of the porosifier mentioned above.

The specific surface area of the porous polymer particles is preferably 30 m$^2$/g or more. From the viewpoint of higher practical usability, the specific surface area is more preferably 35 m$^2$/g or more, and even more preferably 40 m$^2$/g or more. When the specific surface area is 30 m$^2$/g or more, the adsorption amount of the substance to be separated tends to increase. The upper limit of the specific surface area of the porous polymer particles is not particularly limited; however, for example, the specific surface area can be adjusted to be 200 m$^2$/g or less and 100 m$^2$/g or less.

(Coating Layer)

The coating layer of the present embodiment comprises a macromolecule having hydroxyl groups. When the porous polymer particles are coated with a macromolecule having hydroxyl groups, increase in the column pressure can be suppressed, non-specific adsorption of proteins can also be suppressed, and the protein adsorption amount of the separation material tends to improve. Furthermore, when the macromolecule having hydroxyl groups is crosslinked, the increase in the column pressure can be further suppressed.

(Macromolecule Having Hydroxyl Group)

It is preferable that the macromolecule having hydroxyl groups has two or more hydroxyl groups in one molecule, and it is more preferable that the macromolecule having hydroxyl groups is a hydrophilic macromolecule. Examples of the macromolecule having hydroxyl groups include polysaccharides and polyvinyl alcohol. Preferred examples of the polysaccharides include agarose, dextran, cellulose, and chitosan. As the macromolecule having hydroxyl groups, for example, a macromolecule having a weight average molecular weight of about 10,000 to 200,000 can be used.

It is preferable that the macromolecule having hydroxyl groups is a modification product that has been modified with a hydrophobic group, from the viewpoint of enhancing the interface adsorption capacity. Examples of the hydrophobic group include an alkyl group having 1 to 6 carbon atoms, and an aryl group having 6 to 10 carbon atoms. Examples of the alkyl group having 1 to 6 carbon atoms include a methyl group, an ethyl group, and a propyl group. Examples of the aryl group having 6 to 10 carbon atoms include a phenyl group and a naphthyl group. A hydrophobic group can be introduced by causing a compound that has a functional group which reacts with a hydroxyl group (for example, an epoxy group) and a hydrophobic group (for example, glycidyl phenyl ether), to react with the macromolecule having hydroxyl groups by a conventionally known method.

(Method for Forming Coating Layer)

The coating layer that comprises a macromolecule having hydroxyl groups can be formed by, for example, a method disclosed below.

First, a solution of a macromolecule having hydroxyl groups is adsorbed onto the surface of porous polymer particles. The solvent for the solution of a macromolecule having hydroxyl groups is not particularly limited as long as the solvent can dissolve the macromolecule having hydroxyl groups; however, water is most general. The concentration of the macromolecule that is dissolved in the solvent is preferably 5 to 20 (mg/mL).

This solution is impregnated into the porous polymer particles. Regarding the method for impregnation, the porous polymer particles are added to the solution of a macromolecule having hydroxyl groups, and the solution is left to stand for a certain time. The impregnation time may vary depending on the surface state of the porous body;

however, usually, when impregnation is carried out for one day and one night, the macromolecule concentration in the interior of the porous body reaches an equilibrium state with the external concentration. Subsequently, the porous body is washed with a solvent such as water or an alcohol, and any unadsorbed portion of the macromolecule having hydroxyl groups is removed.

(Crosslinking Treatment)

Next, a crosslinking agent is added thereto, and the macromolecule having hydroxyl groups that has adsorbed onto the surface of the porous polymer particles is subjected to a crosslinking reaction. Thus, a crosslinked product is formed. At this time, the crosslinked product has a three-dimensionally crosslinked network structure having hydroxyl groups.

Examples of the crosslinking agent include compounds each having two or more functional groups that are active on a hydroxyl group, such as epihalohydrins such as epichlorohydrin; dialdehyde compounds such as glutaraldehyde; diisocyanate compounds such as methylene diisocyanate; and glycidyl compounds such as ethylene glycol diglycidyl ether. Furthermore, in a case in which a compound having amino groups, such as chitosan, is used as the macromolecule having hydroxyl groups, a dihalide such as dichlorooctane can also be used as the crosslinking agent.

For this crosslinking reaction, a catalyst is usually used. Regarding the catalyst, a conventionally known catalyst can be used as appropriate in accordance with the type of the crosslinking agent; however, for example, in a case in which the crosslinking agent is epichlorohydrin, an alkali such as sodium hydroxide is effective, and in the case of a dialdehyde compound, a mineral acid such as hydrochloric acid is effective.

The crosslinking reaction by a crosslinking agent is usually carried out by adding a crosslinking agent to a system in which the separation material has been dispersed and suspended in an appropriate medium. Regarding the amount of addition of the crosslinking agent, in a case in which a polysaccharide is used as the macromolecule having hydroxyl groups, when one unit of a monosaccharide is regarded as one mole, the amount of addition can be selected according to the performance of the separation material, for example, within the range of 0.1 to 100 times the molar amount of the monosaccharide. Generally, when the amount of addition of the crosslinking agent is reduced, there is a tendency that the coating layer is easily detached from the porous polymer particles. Furthermore, in a case in which the amount of addition of the crosslinking agent is in excess, and the reaction ratio with the macromolecule having hydroxyl groups is high, the characteristics of the macromolecule having hydroxyl groups as a raw material tend to be impaired.

The amount of use of the catalyst may vary with the type of the crosslinking agent; however, usually in a case in which a polysaccharide is used as the macromolecule having hydroxyl groups, when one unit of the monosaccharide that forms the polysaccharide is regarded as one mole, the catalyst is used preferably in an amount in the range of 0.01 to 10 times, and more preferably 0.1 to 5 times, the molar amount of this monosaccharide.

For example, when temperature conditions are employed as the crosslinking reaction conditions, when the temperature of the reaction system is raised, and the temperature reaches the reaction temperature, a crosslinking reaction occurs.

Regarding a specific example of the medium in which the porous polymer particles that have been impregnated with a solution of a macromolecule having hydroxyl groups are dispersed and suspended, it is necessary that the medium does not extract a macromolecule, a crosslinking agent and the like from the macromolecule solution that has been impregnated, and is inactive to the crosslinking reaction. Specific examples of the medium include water and alcohols.

The crosslinking reaction is usually carried out at a temperature in the range of 5° C. to 90° C. for 1 to 10 hours. Preferably, the reaction is carried out at a temperature in the range of 30° C. to 90° C.

After completion of the crosslinking reaction, when the particles thus produced are separated by filtration and then washed with water or a hydrophilic organic solvent such as methanol or ethanol, and any unreacted macromolecule, the medium for suspending, and the like are removed, a separation material in which at least a portion of the surface of porous polymer particles is covered by a coating layer comprising a macromolecule having hydroxyl groups is able to be obtained. It is preferable that the separation material of the present embodiment comprises 30 to 500 mg of the coating layer per 1 g of the porous polymer particles, and it is more preferable that the separation material comprises 30 to 300 mg of the coating layer. The amount of the coating layer can be measured from weight reduction after thermal decomposition, or the like.

(Introduction of Ion Exchanging Group)

The separation material that comprises a coating layer can be used for ion exchange purification, affinity purification and the like, by introducing an ion exchanging group, a ligand (Protein A) or the like via a hydroxyl group or the like on the surface. As a method for introducing an ion exchanging group, for example, a method of using a halogenated alkyl compound may be mentioned.

Examples of the halogenated alkyl compound include a monohalogenocarboxylic acid such as a monohalogenoacetic acid or a monohalogenopropionic acid, and a sodium salt thereof; a primary, secondary or tertiary amine having at least one halogenated alkyl group, such as diethylaminoethyl chloride; and hydrochloride of a quaternary ammonium having a halogenated alkyl group. These halogenated alkyl compounds are preferably bromides or chlorides. The amount of use of the halogenated alkyl compound is preferably 0.2% by mass or more with respect to the total mass of the separation material to which an ion exchanging group is imparted.

For the introduction of an ion exchanging group, it is effective to use an organic solvent in order to accelerate the reaction. Examples of the organic solvent include alcohols such as ethanol, 1-propanol, 2-propanol, 1-butanol, isobutanol, 1-pentanol, and isopentanol.

Since the introduction of an ion exchanging group is usually carried out into a hydroxyl group on the separation material surface, particles in a wet state are dehydrated by filtration or the like, and then the particles are immersed in an alkaline aqueous solution at a predetermined concentration and are left to stand for a certain time. Subsequently, the halogenated alkyl compound is added and reacted in a water-organic solvent mixed system. It is preferable that this reaction is performed at a temperature of 40° C. to 90° C. for 0.5 to 12 hours. The ion exchanging group to be provided is determined based on the type of the halogenated alkyl compound used for the above-described reaction.

As a method for introducing an amino group, which is a weakly basic group, as the ion exchanging group, a method of reacting, among the above-mentioned halogenated alkyl compounds, a mono-, di- or trialkylamine, a mono-, di- or trialkanolamine, a mono-alkyl-mono-alkanolamine, a dialkyl-mono-alkanolamine, a mono-alkyl-di-alkanolamine, or the like, all of which have at least one alkyl group in which some of hydrogen atoms have been substituted by chlorine atoms, may be mentioned. The amount of use of these halogenated alkyl compounds is preferably 0.2% by mass or more with respect to the total mass of the separation material. The reaction conditions are preferably 40° C. to 90° C. and 0.5 to 12 hours.

As a method for introducing a quaternary ammonium group, which is a strongly basic group, as the ion exchanging group, a method of first introducing a tertiary amino group, reacting the tertiary amino group with a halogenated alkyl compound such as epichlorohydrin, and converting the tertiary amino group into a quaternary ammonium group, may be mentioned. Furthermore, hydrochloride of a quaternary ammonium or the like may also be reacted with the separation material.

As a method for introducing a carboxyl group, which is a weakly acidic group, as the ion exchanging group, a method of reacting a monohalogenocarboxylic acid such as a monohalogenoacetic acid or a monohalogenopropionic acid, or a sodium salt thereof as the halogenated alkyl compound, may be mentioned. The amount of use of these halogenated alkyl compounds is preferably 0.2% by mass or more with respect to the total mass of the separation material into which the ion exchanging group is introduced.

As a method for introducing a sulfonic acid group, which is a strongly acidic group, as the ion exchanging group, a method of reacting the separation material with a glycidyl compound such as epichlorohydrin, and adding the separation material to a saturated aqueous solution of a sulfurous acid salt or a bisulfurous acid salt, such as sodium sulfite or sodium bisulfite, may be mentioned. The reaction conditions are preferably 30° C. to 90° C. and 1 to 10 hours.

Meanwhile, as a method for introducing an ion exchanging group, a method of reacting the separation material with 1,3-propanesultone in an alkaline atmosphere may also be mentioned. It is preferable to use 1,3-propanesultone in an amount of 0.4% by mass or more with respect to the total mass of the separation material. The reaction conditions are preferably 0° C. to 90° C. and 0.5 to 12 hours.

The degree of hygroscopicity of the separation material of the present embodiment is measured by the following method. 1 g of a dry separation material is left to stand for 18 hours in a constant temperature constant humidity test chamber (temperature 60° C., humidity 90%), and then the mass of the separation material is measured again. Thereby, the degree of hygroscopicity is calculated by the following formula.

(Separation material mass after moisture absorption−1)g/1 g×100=Degree of hygroscopicity (%)

The degree of hygroscopicity of the separation material of the present embodiment is preferably 1% to 30% by mass, more preferably 1% to 20% by mass, and even more preferably 1% to 10% by mass. When the degree of hygroscopicity of the separation material is 30% by mass or less, the decrease in liquid permeability of the separation material due to the thickness of the coating layer can be suppressed.

The average pore size, the mode diameter in the pore size distribution, the specific surface area, and the porosity of the separation material or porous polymer particles of the present embodiment are values measured with a mercury intrusion analyzer (AUTOPORE; manufactured by Shimadzu Corp.), and these are measured as follows. 0.05 g of a sample is added to a standard 5-mL cell for powder (stem volume 0.4 mL), and measurement is made under the conditions of an initial pressure of 21 kPa (about 3 psia, equivalent to a pore diameter of about 60 μm). The mercury parameter is set to have a mercury contact angle of 130 degrees, which is an apparatus default value, and a mercury surface tension of 485 dynes/cm. Furthermore, the respective values are calculated with limiting the pore size to the range of 0.1 to 3 μm.

The separation material of the present embodiment is suitable for the use in separation of a protein by electrostatic interaction and affinity purification. For example, when the separation material of the present embodiment is added to a mixed solution including a protein, only the protein is adsorbed onto the separation material by electrostatic interaction, and then the separation material is separated by filtration from the solution and is added to an aqueous solution having a high salt concentration, the protein that has adsorbed to the separation material can be easily released and collected. Furthermore, the separation material of the present embodiment can also be used for column chromatography. An embodiment of a separatory column is illustrated in FIG. 1. The separatory column 10 comprises a column 1 and a separation material 2 packed in the column 1.

As a bio-macromolecule that can be separated by using the separation material of the present embodiment, a water-soluble substance is preferred. Specific examples of bio-macromolecules include proteins, such as blood proteins such as serum albumin and immunoglobulin; enzymes present in the living body; protein physiologically active substances produced by biotechnologies; and DNA and physiologically active peptides. The weight average molecular weight is preferably 2,000,000 or less, and more preferably 500,000 or less. Furthermore, it is necessary to select, according to known methods, the properties of the separation material, conditions and the like based on the isoelectric point, ionization state and the like of the protein. As the known methods, for example, the method described in JP S60-169427 A may be mentioned.

The separation material of the present embodiment has the respective advantages of particles formed from a natural macromolecule or particles formed from a synthetic macromolecule in connection with the separation of a bio-macromolecule such as a protein, by subjecting the coating layer on the porous polymer particles to a crosslinking treatment, and then introducing an ion exchanging group, Protein A or the like into the surface of the separation material. Particularly, since the porous polymer particles in the separation material of the present embodiment are particles that are obtained by the method described above, the porous polymer particles have durability and alkali resistance. Furthermore, the separation material of the present embodiment has a tendency that non-specific adsorption of proteins is reduced, and adsorption and desorption of proteins easily occurs. Furthermore, the separation material of the present embodiment has a tendency that the adsorption amount of a protein or the like under the same flow rate (dynamic adsorption amount) is large.

The liquid permeation rate according to the present embodiment represents the liquid permeation rate at the time when the separation material of the present embodiment is packed in a stainless steel column having a size of ϕ7.8×300 mm, and a liquid is passed therethrough. In a case in which the separation material of the present embodiment is packed in a column, it is preferable that when the column pressure is 0.3 MPa, the liquid permeation rate is 800 cm/h or higher. In a case in which separation of a protein is performed by column chromatography, the liquid permeation rate of a protein solution or the like is generally in the range of 400 cm/h or less; however, in a case in which the separation material of the present embodiment is used, the separation material can be used at a liquid permeation rate of 800 cm/h or higher, which is faster than those of conventional separation materials for protein separation.

The average particle size of the separation material of the present embodiment is preferably 10 to 500 μm, and more preferably 10 to 300 μm. For the use in preparative or industrial chromatography, in order to avoid an extreme increase in the column internal pressure, the average particle size is preferably 10 to 100 μm.

In a case in which the separation material of the present embodiment is used as a column packing material in column chromatography, since there is hardly any volume change within the column independently of the properties of the eluent used, operability is excellent.

The 5% compressive deformation modulus of the separation material of the present embodiment can be calculated as follows.

The load and compression displacement at the time when particles are compressed up to 50 mN by means of a smooth cross-section (50 μm×50 μm) of a quadrangular prism at a load loading rate of 1 mN/sec under the conditions of room temperature (25° C.), by using a microcompression testing machine (manufactured by Fisher Scientific Co., LLC). The compression modulus (5% K value) at the time when the particles have undergone 5% compressive deformation can be determined from the measurement values thus obtained, by the formula described below. The load at the point where the amount of displacement undergoes the largest change during the measurement is designated as the breaking strength (mN).

$$5\% \ K \text{ value (MPa)} = (3/2^{1/2}) \cdot F \cdot S^{-3/2} \cdot R^{-1/2}$$

F: Load (mN) at the time when crosslinked polymer particles have undergone 40% compressive deformation S: Compression displacement (mm) at the time when crosslinked polymer particles have undergone 40% compressive deformation R: Radius (mm) of crosslinked polymer particles The compression modulus (5% K value) at the time when the separation material is subjected to 5% compressive deformation is 100 to 1,000 MPa, preferably 200 to 1,000 MPa, and more preferably 250 to 1,000 MPa.

When the compression modulus is less than 100 MPa, flexibility of the porous polymer particles increases, and when a liquid is allowed to flow through the column, the separation material is easily deformed, while the column pressure is likely to increase.

The pore volume (porosity) of the separation material is preferably 30% by volume or more, more preferably from 30% by volume to 70% by volume, and even more preferably from 40% by volume to 70% by volume, based on the total volume (including the pore volume) of the separation material. It is preferable that the separation material has pores having a pore size of 0.1 to 0.5 μm, that is, macropores (macrovoids). The mode diameter in the pore size distribution (most frequent value of the pore size distribution, maximum frequency pore size, average pore size) of the separation material is 0.1 to 0.5 μm, and preferably 0.2 to 0.5 μm. When the mode diameter in the pore size distribution is 0.1 μm or larger, there is a tendency that substances can easily enter into the pores, and when the mode diameter in the pore size distribution is 0.5 μm or less, the specific surface area becomes sufficient.

The specific surface area of the separation material is preferably 30 m²/g or more. From the viewpoint of higher practical usability, the specific surface area is more preferably 35 m²/g or more, and even more preferably 40 m²/g or more. When the specific surface area is 30 m²/g or more, the adsorption amount of the substance to be separated tends to increase. The upper limit of the specific surface area of the separation material is not particularly limited; however, for example, the specific surface area can be adjusted to 200 m²/g or less, and 100 m²/g or less.

The 5% deformation modulus, the average pore size, the mode diameter in the pore size distribution, the specific surface area and the like of the separation material can be adjusted by appropriately selecting the ingredients of the porous polymer particles, the porosifier, the macromolecule having hydroxyl groups, and the like.

In the present embodiment, a separation material in the form of having an ion exchanging group introduced thereinto has been explained; however, even if an ion exchanging group is not introduced, the separation material can be used as a separation material. Such a separation material can be utilized in, for example, gel permeation chromatography. That is, the separatory column of the present embodiment comprises a column and the separation material of the present embodiment packed in the column.

When the separation material according to the first embodiment is used, a separation material that reduces non-specific adsorption of proteins, has excellent alkali resistance and durability, and has excellent column characteristics such as liquid permeability when used as a column, can be provided.

Second Embodiment and Third Embodiment

Separatory material according to a second embodiment and a third embodiment will be explained below. The separation material of the present embodiment comprises porous polymer particles; and a coating layer that covers at least a portion of the surface of the porous polymer particles, and the coating layer comprises a macromolecule having hydroxyl groups. In the present embodiment, the "surface of the porous polymer particles" is meant to include not only the external surface of the porous polymer particles, but also the surface of pores in the interior of the porous polymer particles. For example, the external surface of the porous polymer particles, and/or the surface of pores in the interior of the porous polymer particles may be coated with the macromolecule having hydroxyl groups.

(Porous Polymer Particles)

The porous polymer particles of the present embodiment comprises, for example, a polymer that is obtained by polymerizing monomers, and can have structural units derived from the monomers. The porous polymer particles may include 50% by mass or more of a polymer based on the total mass of the particles, or may be particles consist of a polymer. The porous polymer particles can be obtained by polymerizing a composition including monomers and a porosifier, and then eliminating the porosifier. The porous polymer particles can be synthesized by, for example, conventional suspension polymerization or emulsion polymerization or the like. There are no particular limitations on the monomers, and for example, vinyl monomers such as a (meth)acrylic monomer and a styrene-based monomer can be used. Specific examples of the monomers include polyfunctional monomers and monofunctional monomers such as described below.

Examples of polyfunctional monomers include divinyl compounds such as divinylbenzene, divinylbiphenyl, divinylnaphthalene, and divinylphenanthrene; (poly)alkylene glycol-based di(meth)acrylates such as (poly)ethylene glycol di(meth)acrylate, (poly)propylene glycol di(meth)acrylate, and (poly)tetramethylene glycol di(meth)acrylate; trifunctional or higher-functional (meth)acrylates such as trimethylolpropane tri(meth)acrylate, tetramethylolmethane tri(meth)acrylate, tetramethylolpropane tetra(meth)acrylate, pentaerythritol tri(meth)acrylate, 1,1,1-trishydroxymethylethane tri(meth)acrylate, and 1,1,1-trishydroxymethylpropane triacrylate; di(meth)acrylates such as ethoxylated bisphenol A-based di(meth)acrylate, propoxylated ethoxylated bisphenol A-based di(meth)acrylate, tricyclodecanedimethanol di(meth)acrylate, 1,1,1-trishydroxymethylethane di(meth)acrylate, and ethoxylated cyclohexanedimethanol di(meth)acrylate; diallyl phthalate and isomers thereof; and triallyl isocyanurate and derivatives thereof. As the polyfunctional monomers, NK ESTER (A-TMPT-6PO, A-TMPT-3EO, A-TMM-3LMN, A-GLY series, A-9300, AD-TMP, AD-TMP-4CL, ATM-4E, A-DPH, and the like) manufactured by Shin Nakamura Chemical Co., Ltd.; divinylbenzene (DVB960) of Nippon Steel & Sumikin Chemical Co., Ltd.; and the like are commercially available. The polyfunctional monomers can be used singly or in combination of two or more kinds thereof.

Among those described above, from the viewpoint of having excellent durability, acid resistance, alkali resistance, and swellability, it is preferable to use divinylbenzene. In a case in which the monomers include divinylbenzene, the content of divinylbenzene is preferably 50% by mass or more, more preferably 60% by mass or more, even more preferably 70% by mass or more, and still more preferably 80% by mass or more, based on the total mass of the monomers, from the viewpoint of having superior durability, acid resistance, alkali resistance, and swellability.

Examples of monofunctional monomers include styrene and derivatives thereof, such as styrene, o-methylstyrene, m-methylstyrene, p-methylstyrene, α-methylstyrene, o-ethylstyrene, m-ethylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, and 3,4-dichlorostyrene; (meth)acrylic acid esters such as methyl acrylate, ethyl acrylate, propyl acrylate, n-butyl acrylate, isobutyl acrylate, hexyl acrylate, 2-ethylhexyl acrylate, n-octyl acrylate, dodecyl acrylate, lauryl acrylate, stearyl acrylate, 2-chloroethyl acrylate, phenyl acrylate, methyl α-chloroacrylate, methyl methacrylate, ethyl methacrylate, propyl methacrylate, n-butyl methacrylate, isobutyl methacrylate, hexyl methacrylate, 2-ethylhexyl methacrylate, n-octyl methacrylate, dodecyl methacrylate, lauryl methacrylate, and stearyl methacrylate; vinyl esters such as vinyl acetate, vinyl propionate, vinyl benzoate, and vinyl butyrate; N-vinyl compounds such as N-vinylpyrrole, N-vinylcarbazole, N-vinylindole, and N-vinylpyrrolidone; fluorine-containing monomers such as vinyl fluoride, vinylidene fluoride, tetrafluoroethylene, hexafluoropropylene, trifluoroethyl acrylate, and tetrafluoropropyl acrylate; and conjugated dienes such as butadiene and isoprene. The monofunctional monomers can be used singly or in combination of two or more kinds thereof. Among those described above, from the viewpoint of having excellent acid resistance and alkali resistance, it is preferable to use styrene. Furthermore, styrene derivatives having functional groups such as a carboxyl group, an amino group, a hydroxyl group, and an aldehyde group can also be used.

Examples of the porosifier include aliphatic or aromatic hydrocarbons, esters, ketones, ethers, and alcohols, which are organic solvents that accelerate phase separation at the time of polymerization and accelerate porosification of particles. Specific examples include toluene, diethylbenzene, xylene, cyclohexane, octane, butyl acetate, dibutyl phthalate, methyl ethyl ketone, dibutyl ether, 1-hexanol, isoamyl alcohol, 2-octanol, decanol, lauryl alcohol, and cyclohexanol. The porosifiers can be used singly or in combination of two or more kinds thereof.

In a case in which a substance that can be easily incorporated into water is used as the porosifier, it is preferable to use the substance because large pores are easily opened in the interior of particles. Examples of such a porosifier include alcohols.

The porosifier can be used in an amount of 0% to 250% by mass based on the total mass of the monomers. Porosity of the porous polymer particles can be controlled by the amount of the porosifier. Furthermore, the size and shape of the pores of the porous polymer particles can be controlled by the type of the porosifier.

The porosifier can be used in an amount of 0% to 250% by mass based on the total mass of the monomers, and it is preferable to use the porosifier in an amount of 0% to 200% by mass. Porosity of the porous polymer particles can be controlled by the amount of the porosifier. Furthermore, the size and shape of the pores of the porous polymer particles can be controlled by the type of the porosifier.

Furthermore, water that is used as a solvent can also be used as the porosifier. In a case in which water is used as the porosifier, water can be absorbed by dissolving an oil-soluble surfactant (emulsifier) in the monomers, and particles can be easily porosified.

Examples of the oil-soluble surfactant include sorbitan monoesters of a branched C16-C24 fatty acid, a linear unsaturated C16-C22 fatty acid or a linear saturated C12-C14 fatty acid (for example, sorbitan monolaurate, sorbitan monooleate, sorbitan monomyristate, or a sorbitan monoester derived from coconut fatty acids); a diglycerol monoester (for example, diglycerol monooleate (for example, diglycerol monooleate of a C18:1 (number of carbon atoms: 18, number of double bonds: 1) fatty acid), diglycerol monomyristate, diglycerol monoisostearate, or diglycerol monoester of coconut fatty acids) of a branched C16-C24 fatty acid, a linear unsaturated C16-C22 fatty acid or a linear saturated C12-C14 fatty acid; a diglycerol monoaliphatic ether of a branched C16-C24 alcohol (for example, Guerbet alcohol), a linear unsaturated C16-C22 alcohol, or a linear saturated C12-C14 alcohol (for example, coconut fatty alcohol); and mixtures of these emulsifiers.

Preferred examples of the oil-soluble surfactant include sorbitan monolaurate (for example, SPAN (registered trademark) 20, sorbitan monolaurate preferably having a purity of higher than about 40%, more preferably a purity of higher than about 50%, and most preferably a purity of higher than about 70%); sorbitan monooleate (for example, SPAN (registered trademark) 80, sorbitan monooleate preferably having a purity of higher than about 40%, more preferably a purity of higher than about 50%, and most preferably a purity of higher than about 70%); diglycerol monooleate (for example, diglycerol monooleate preferably having a purity of higher than about 40%, more preferably a purity of higher than about 50%, and most preferably a purity of higher than about 70%); diglycerol monoisostearate (for example, diglycerol monoisostearate preferably having a purity of higher than about 40%, more preferably a purity of higher than about 50%, and most preferably a purity of higher than about 70%); diglycerol monomyristate (sorbitan monomyristate preferably having a purity of higher than about 40%, more preferably a purity of higher than about 50%, and most preferably a purity of higher than about 70%); cocoyl (for example, a lauryl group or a myristoyl group) ether of diglycerol; and mixtures of these.

It is preferable to use the oil-soluble surfactant in an amount in the range of 5% to 80% by mass based on the total mass of the monomers. When the content of the oil-soluble surfactant is 5% by mass or more, since stability of water droplets becomes sufficient, large single holes are not easily formed. When the content of the oil-soluble surfactant is 80% by mass or less, it is easier for the porous polymer particles to maintain the shape after polymerization.

A composition for obtaining the porous polymer particles may comprise soluble particles as the porosifier. Soluble particles are particles that can be dissolved in, for example, an acid, an alkali, or a solvent. The soluble particles do not dissolve during polymerization, and can be removed by after particle formation, by a method of dissolving the powdered porosifier by immersing the polymer particles in an acid solution, or the like. As the constituent material for the soluble particles, specifically, calcium carbonate, tricalcium phosphate, silica, a polymer, a metal colloid, and the like can be used. As the constituent material for the soluble particles, it is preferable to use calcium carbonate, tricalcium phosphate or the like, from the viewpoint of the ease of removal. The particle size of the soluble particles is preferably 0.6 to 5 µm. The particle size of the soluble particles is more preferably 1 to 5 µm, from the viewpoint of further enhancing liquid permeability of the separation material. The average particle size of the soluble particles can be measured by a method similar to the method for measuring the average particle size of the porous polymer particles that will be described below.

Examples of an aqueous medium that is used for the polymerization reaction include water, and a mixed medium of water and a water-soluble solvent (for example, a lower alcohol). A surfactant may be included in the aqueous medium. As the surfactant, all of anionic, cationic, nonionic, and zwitterionic surfactants can be used.

Examples of anionic surfactants include fatty acid oils such as sodium oleate and castor oil potassium; alkyl sulfuric acid ester salts such as sodium lauryl sulfate and ammonium lauryl sulfate; alkyl benzenesulfonic acid salts such as sodium dodecyl benzenesulfonate; alkyl naphthalenesulfonic acid salts; alkane sulfonic acid salts, dialkyl sulfosuccinic acid salts such as sodium dioctyl sulfosuccinate; alkenyl succinic acid salts (dipotassium salts); alkyl phosphoric acid ester salts; naphthalenesulfonic acid-formalin condensate; polyoxyethylene alkyl phenyl ether sulfuric acid ester salts; polyoxyethylene alkyl ether sulfuric acid salts such as sodium polyoxyethylene lauryl ether sulfate; and polyoxyethylene alkyl sulfuric acid ester salts.

Examples of cationic surfactants include alkyl amine salts such as lauryl amine acetate and stearyl amine acetate; and quaternary ammonium salts such as lauryl trimethylammonium chloride.

Examples of nonionic surfactants include hydrocarbon-based nonionic surfactants such as polyethylene glycol alkyl ethers, polyethylene glycol alkyl aryl ethers, polyethylene glycol esters, polyethylene glycol sorbitan esters, and polyalkylene glycol alkyl amines or amides; polyether-modified silicone-based nonionic surfactants such as polyethylene oxide adducts and polypropylene oxide adducts of silicones; and fluorine-based nonionic surfactants such as perfluoroalkyl glycols.

Examples of zwitterionic surfactants include hydrocarbon surfactants such as lauryl dimethylamine oxide; phosphoric acid ester-based surfactants; and phosphorous ester-based surfactants.

The surfactants may be used singly or in combination of two or more kinds thereof. Among the surfactants described above, from the viewpoint of having excellent dispersion stability at the time of polymerizing the monomers, an anionic surfactants are preferred.

Examples of a polymerization initiator that is added as necessary include organic peroxides such as benzoyl peroxide, lauroyl peroxide, benzoyl orthochloroperoxide, benzoyl orthomethoxyperoxide, 3,5,5-trimethylhexanoyl peroxide, tert-butyl peroxy-2-ethylhexanoate, and di-tert-butyl peroxide; and azo-based compounds such as 2,2'-azobisisobutyronitrile, 1,1'-azobiscyclohexanecarbonitrile, and 2,2'-azobis(2,4-dimethylvaleronitrile). The polymerization initiator can be used in an amount in the range of 0.1 to 7.0 parts by mass with respect to 100 parts by mass of the monomers.

The polymerization temperature can be appropriately selected according to the types of the monomers and the polymerization initiator. The polymerization temperature is preferably 25° C. to 110° C., and more preferably 50° C. to 100° C.

In regard to the synthesis (polymerization process) of the porous polymer particles, a macromolecule dispersion stabilizer may be used in order to enhance the dispersion stability of the particles, or a macromolecule dispersion stabilizer may be added to the emulsion liquid.

Examples of the macromolecule dispersion stabilizer include polyvinyl alcohol, polycarboxylic acids, celluloses (hydroxyethyl cellulose, carboxymethyl cellulose, methyl cellulose, and the like), and polyvinylpyrrolidone, and inorganic water-soluble macromolecule compounds such as sodium tripolyphosphate can also be used in combination. Among these, polyvinyl alcohol or polyvinylpyrrolidone is preferred. The amount of addition of the macromolecule dispersion stabilizer is preferably 1 to 10 parts by mass with respect to 100 parts by mass of the monomers.

In order to prevent the monomers from being polymerized alone (for example, in order to suppress the generation of particles by emulsion polymerization of monomers alone in water), water-soluble polymerization inhibitors such as nitrous acid salts, sulfurous acid salts, hydroquinones, ascorbic acids, water-soluble vitamin B compounds, citric acid, and polyphenols may also be used.

The average particle size of the porous polymer particles is preferably 500 µm or less, more preferably 300 µm or less, even more preferably 150 µm or less, still more preferably 120 µm or less, and particularly preferably 100 µm or less. Furthermore, the average particle size of the porous polymer particles is preferably 10 µm or more, more preferably 30 µm or more, and even more preferably 50 µm or more, from the viewpoint of further enhancing liquid permeability and from the viewpoint of suppressing an increase in the column pressure after column packing.

The pore volume (porosity) of the porous polymer particles is preferably 30% to 70% by volume, more preferably 40% to 70% by volume, and even more preferably 50% to 70% by volume, based on the total volume of the porous polymer particles. It is preferable that the porous polymer particles have pores having a pore size (mode diameter) of 0.01 µm or more and less than 0.6 µm, that is, macropores (macrovoids). The pore size is more preferably 0.1 µm or more and less than 0.5 µm, and even more preferably 0.2 µm or more and less than 0.5 µm. When the pore size is 0.01 µm or more, there is a tendency that substances can easily enter into the pores, and when the pore size is less than 0.6 μm, the specific surface area becomes sufficient. These can be adjusted by means of the porosifier described above.

The coefficient of variation (C.V.) of the particle size of the porous polymer particles is preferably 3% to 15%, more preferably 5% to 15% or 3% to 12%, even more preferably 3% to 10%, and still more preferably 5% to 10%, from the viewpoint of further enhancing liquid permeability. As a method for decreasing the C.V., a method of monodispersing the porous polymer particles by means of an emulsifying apparatus such as a MICRO PROCESS SERVER (for example, manufactured by Hitachi, Ltd.) may be mentioned.

The specific surface area of the porous polymer particles is preferably 30 m$^2$/g or more. When the specific surface area is 30 m$^2$/g or more, the adsorption amount of the substance to be separated tends to increase. The specific surface area of the porous polymer particles is more preferably 35 m$^2$/g or more, and even more preferably 40 m$^2$/g or more, from the viewpoint of higher practical usability.

(Coating Layer)

The coating layer of the present embodiment comprises a macromolecule having hydroxyl groups (for example, a water-soluble macromolecule). By coating the porous polymer particles with a macromolecule having hydroxyl groups, an increase in the column pressure can be suppressed and also, non-specific adsorption of proteins can be suppressed. Furthermore, the protein adsorption amount of the separation material can be made equivalent to or higher than the protein adsorption amount in the case of using a natural macromolecule. Furthermore, if the macromolecule having hydroxyl groups is crosslinked, an increase in the column pressure can be further suppressed.

It is preferable that macromolecule having hydroxyl groups has two or more hydroxyl groups in one molecule. Furthermore, it is preferable that the macromolecule having hydroxyl groups is a hydrophilic macromolecule. Examples of the macromolecule having hydroxyl groups include polysaccharides (agarose, dextran, cellulose, polyvinyl alcohol, chitosan, and the like), and macromolecules respectively having a weight average molecular weight of about 10,000 to 200,000 can be used.

Furthermore, as the macromolecule having hydroxyl groups, a modification product modified with a hydrophobic group (modification product in which a hydrophobic group has been introduced, or the like) can be used from the viewpoint of increasing the interface adsorption capacity. Examples of the hydrophobic group include an alkyl group having 1 to 6 carbon atoms, and an aryl group having 6 to 10 carbon atoms. Examples of the alkyl group having 1 to 6 carbon atoms include a methyl group, an ethyl group, and a propyl group. Examples of the aryl group having 6 to 10 carbon atoms include a phenyl group and a naphthyl group. The hydrophobic group can be introduced by reacting a compound having a functional group that reacts with a hydroxyl group (an epoxy group or the like) and having a hydrophobic group (glycidyl phenyl ether or the like), with a macromolecule having hydroxyl groups by a conventionally known method. Examples of such a modification product include modification products of polysaccharides, and specific examples include a modification product of agarose (modified agarose), a modification product of dextran, a modification product of cellulose, a modification product of polyvinyl alcohol, and a modification product of chitosan.

[Method for Forming Coating Layer]

The coating layer that comprises a macromolecule having hydroxyl groups can be formed by, for example, a method described below. The coating layer can be formed by coating the porous polymer particles with a macromolecule having hydroxyl groups. As a method for forming the coating layer, for example, a method of adsorbing a solution of a macromolecule having hydroxyl groups onto the surface of the porous polymer particles, removing any unadsorbed portion, subsequently performing a crosslinking reaction by means of a crosslinking agent, and making the macromolecule having hydroxyl groups stick in the pores, may be mentioned. The solvent for the solution of the macromolecule having hydroxyl groups is not particularly limited as long as the solvent can dissolve the macromolecule having hydroxyl groups; however, water is most general. The concentration of the macromolecule that dissolves in the solvent is preferably 5 to 20 mg/mL.

This solution is impregnated into the porous polymer particles. As a method for impregnation, a method of adding the porous polymer particles to a solution of the macromolecule having hydroxyl groups, and leaving the solution to stand for a certain time, may be mentioned. The impregnation time also varies depending on the surface state of the porous polymer particles; however, usually, when impregnation is carried out for one day and one night, the macromolecule concentration in the interior of the porous polymer particles reaches an equilibrium state with the external concentration. Subsequently, the particles are washed with a solvent such as water or an alcohol, any unadsorbed portion of the macromolecule having hydroxyl groups is removed.

[Crosslinking Treatment]

Next, a crosslinking agent is added thereto, subsequently the macromolecule having hydroxyl groups that has adsorbed onto the surface of the porous polymer particles is subjected to a crosslinking reaction, and thereby, a crosslinked product is formed. For example, a crosslinking agent is added, subsequently the macromolecule having hydroxyl groups that has adsorbed onto the surface of the porous polymer particles is subjected to a crosslinking reaction, and thereby a crosslinked gel of the polymer is formed. At this time, in the crosslinked product, for example, the macromolecule having hydroxyl groups has a three-dimensional crosslinked network structure.

Examples of the crosslinking agent include compounds each having two or more functional groups that are active on a hydroxyl group (OH group), such as an epihalohydrin such as epichlorohydrin; a dialdehyde compound such as glutaraldehyde; a diisocyanate compound such as methylene diisocyanate; and a glycidyl compound such as ethylene glycol diglycidyl ether. Furthermore, in a case in which a compound having amino groups, such as chitosan, is used as the macromolecule having hydroxyl groups, a dihalide such as dichlorooctane can also be used as a crosslinking agent.

A catalyst is usually used for this crosslinking reaction, and the catalyst varies with the type of the crosslinking agent. However, for example, in a case in which the crosslinking agent is epichlorohydrin, an alkali such as sodium hydroxide is effective, and in a case in which the crosslinking agent is a dialdehyde compound, a mineral acid such as hydrochloric acid is effective.

The crosslinking reaction by a crosslinking agent can be usually carried out by adding the crosslinking agent to a system in which the separation material before crosslinking has been disperse and suspended in an appropriate medium. Regarding the amount of addition of the crosslinking agent, in a case in which a polysaccharide or a modification product thereof is used as the macromolecule having hydroxyl groups, when one unit of a monosaccharide is regarded as one mole, the amount of addition can be selected according to the intended performance of the separation material, within the range of 0.1 to 100 times the molar amount of the monosaccharide. Generally, when the amount of addition of the crosslinking agent is less than 0.1 times by mole, there is a tendency that the coating layer is easily detached from the porous polymer particles. Furthermore, in a case in which the amount of addition of the crosslinking agent is more than 100 times by mole, and the reaction ratio with the macromolecule having hydroxyl groups is high, the characteristics of the raw material macromolecule having hydroxyl groups tend to be impaired.

The amount of use of a catalyst at the time of a crosslinking reaction may vary depending on the type of the crosslinking agent; however, usually, in a case in which a polysaccharide is used as the macromolecule having hydroxyl groups, when one unit of a monosaccharide that forms the polysaccharide is taken as one mole, the catalyst is used in an amount in the range of 0.01 to 10 times, and more preferably in the range of 0.1 to 5 times, the molar amount of this monosaccharide.

For example, in a case in which temperature conditions are employed as the crosslinking reaction conditions, when the temperature of the reaction system is raised, and the temperature reaches the reaction temperature, a crosslinking reaction occurs.

As a specific example of the medium in which porous polymer particles onto which a solution of a macromolecule having hydroxyl groups or the like has been adsorbed are dispersed and suspended, there are no limitations as long as the medium does not extract the adsorbed macromolecule, the crosslinking agent and the like, and is not inert to the crosslinking reaction. Specific examples of such a medium include water and alcohols.

The crosslinking reaction is usually carried out at a temperature in the range of 5° C. to 90° C. for 1 to 24 hours, or for 1 to 10 hours. Preferably, the temperature is a temperature in the range of 30° C. to 90° C.

After completion of the crosslinking reaction, a composite of the porous polymer particles (porous body) and the crosslinked gel thus produced is separated by filtration, subsequently the composite is washed with water, a hydrophilic organic solvent (methanol, ethanol, or the like) or the like, and any unreacted macromolecule, the medium for suspension, and the like are removed. Then, a separation material in which at least a portion of the surface of the porous polymer particles is coated with a coating layer comprising the macromolecule having hydroxyl groups is obtained. It is preferable that the separation material of the present embodiment comprises 30 to 500 mg of the coating layer per 1 g of the porous polymer particles. The amount of the coating layer is more preferably 30 to 450 mg, and even more preferably 30 to 400 mg, per 1 g of the porous polymer particles. The amount of the coating layer can be measured from weight reduction under thermal decomposition, or the like.

[Introduction of Ion Exchanging Group]

The separation material that comprises a coating layer can be used for ion exchange purification, affinity purification and the like, by introducing an ion exchanging group, a ligand (Protein A) or the like via a hydroxyl group or the like of the particle surface. As a method for introducing an ion exchanging group, for example, a method of using a halogenated alkyl compound (a compound comprising halogenated alkyl group) may be mentioned.

Examples of the halogenated alkyl compound include a monohalogenocarboxylic acid such as a monohalogenoacetic acid or a monohalogenopropionic acid, and a sodium salt thereof; a primary, secondary or tertiary amine having at least one halogenated alkyl group, such as diethylaminoethyl chloride; and hydrochloride of a quaternary ammonium having a halogenated alkyl group. These halogenated alkyl compounds are preferably bromides or chlorides. The amount of use of the halogenated alkyl compound is preferably 0.2% by mass or more based on the total mass of the separation material into which an ion exchanging group is introduced (the separation material before the ion exchanging group is introduced).

Since the introduction of an ion exchanging group is usually performed into a hydroxyl group at the surface of the separation material, particles in a wet state are dehydrated by filtration or the like, and then the particles are immersed in an alkaline aqueous solution at a predetermined concentration and are left to stand for a certain time. Subsequently, the halogenated alkyl compound is added and reacted in water or a water-organic solvent mixed system. As a method for introducing an ion exchanging group, generally, a method of dissolving a hydrophilic natural macromolecule in an aqueous solution of sodium hydroxide, and causing the macromolecule to react with a halogenated alkyl compound in water or a water-organic solvent mixed system, may be mentioned. The amount of use of the halogenated alkyl compound is, for example, 0.2% by mass or more based on the total mass of the hydrophilic natural macromolecule. It is preferable that this reaction is performed at a temperature of 40° C. to 90° C. and under reflux, for 0.5 to 12 hours. The ion exchanging group to be provided is determined based on the type of the halogenated alkyl compound used for the above-described reaction.

As a method for introducing an amino group, which is a weakly basic group, as the ion exchanging group, a method of reacting, among the halogenated alkyl compounds described above, a secondary or tertiary aminohalogenide such as a mono-, di- or trialkyl aminochloride, a mono-, di- or trialkanol aminochloride, or a mono- (or di-)alkyl-mono- (or di-)alkanol aminochloride, or the like may be mentioned. The amount of use of such an amine is, for example, 0.2% by mass or more based on the total mass of the separation material into which the ion exchanging group is introduced. The reaction conditions are, for example, 40° C. to 90° C. and 0.5 to 12 hours.

As a method for introducing a quaternary ammonium group, which is a strongly basic group, as the ion exchanging group, a method of first introducing a tertiary amino group, reacting the tertiary amino group with a halogenated alkyl compound such as epichlorohydrin, and converting the tertiary amino group into a quaternary ammonium group, may be mentioned. Alternatively, a quaternary aminohalogenide such as a quaternary ammonium chloride may also be reacted with the separation material (composite) by a method similar to the case of the primary to tertiary aminochloride mentioned above.

As a method for introducing a carboxyl group, which is a weakly acidic group, as the ion exchanging group, a method of reacting a monohalogenocarboxylic acid such as a monohalogenoacetic acid or a monohalogenopropionic acid, or a sodium salt thereof as the halogenated alkyl compound, may be mentioned. The amount of use of such a halogenated alkyl compound is, for example, 0.2% by mass or more based on the total mass of the separation material into which the ion exchanging group is introduced.

As a method for introducing a sulfonic acid group, which is a strongly acidic group, as the ion exchanging group, a method of reacting the separation material with a glycidyl compound such as epichlorohydrin, and adding the separation material into a saturated aqueous solution of a sulfurous acid salt or a bisulfurous acid salt, such as sodium sulfite or sodium bisulfite, may be mentioned. The reaction conditions are, for example, 30° C. to 90° C. and 1 to 10 hours.

As another method for introducing an ion exchanging group, a method of reacting the separation material with 1,3-propanesultone in an alkaline atmosphere may also be mentioned. 1,3-Propanesultone is used, for example, in an amount of 0.4% by mass or more based on the total mass of the separation material into which the ion exchanging group is introduced. The reaction conditions are, for example, 0° C. to 90° C. and 0.5 to 12 hours.

Examples of the method for introducing an ion exchanging group other than these methods include a method of reacting sulfopropyl, and a method of adding an epihalohydrin diglycidyl compound or the like followed by introducing an ion exchanging group into a glycidyl group.

The pore volume (porosity) of the separation material of the present embodiment may be 30% by volume or more, preferably 40% by volume or more, more preferably 50% by volume or more, even more preferably 40 to 70% by volume, still more preferably 50% to 70% by volume, and particularly preferably 50% to 65% by volume based on the total volume of the separation material. When the pore volume is in these ranges, strength of the particles tends to increase (particles are not easily crushed).

The pore size (mode diameter, most frequent value of the pore size distribution, maximum frequency pore size) of the separation material of the present embodiment is preferably 0.05 to 0.6 μm, more preferably 0.05 to 0.5 μm, and even more preferably 0.1 to 0.5 μm. When the pore size is in these ranges, a liquid can flow easily within the particles, and the dynamic adsorption amount is likely to become large.

The specific surface area of the separation material of the present embodiment is preferably 30 m$^2$/g or more. From the viewpoint of higher practical usability, the specific surface area is more preferably 35 m$^2$/g or more, and even more preferably 40 m$^2$/g or more. When the specific surface is 30 m$^2$/g or more, the adsorption amount of the substance to be separated tends to become large. The upper limit of the specific surface area of the separation material is not particularly limited; however, the specific surface area can be, for example, 300 m$^2$/g or less.

The pore volume, pore diameter (mode diameter), and specific surface area of the separation material or the porous polymer particles of the present embodiment can be measured, for example, as follows by using a mercury intrusion analyzer (AUTOPORE; manufactured by Shimadzu Corp.). About 0.05 g of a sample is introduced into a standard 5-mL cell for powder (stem volume 0.4 mL), and measurement is made under the conditions of an initial pressure of 21 kPa (about 3 psia, equivalent to a pore diameter of about 60 μm). The mercury parameters are set to have a mercury contact angle of 130 degrees, which is an apparatus default value, and a mercury surface tension of 485 dynes/cm. For the pore volume and the specific surface area, the respective values are calculated with limiting the pore size that corresponds to the most frequent value in the pore size distribution (mode diameter) thus obtained, to a pore size in the range of 0.05 to 5 μm.

The average particle size of the separation material of the present embodiment is preferably 10 to 500 μm, and more preferably 30 to 150 μm. For the use in preparative or industrial chromatography, the average particle size is more preferably 50 to 150 μm, and even more preferably 50 to 100 μm, in order to avoid an extreme increase in the column internal pressure.

The average particle size and the C.V. (coefficient of variation) of the particle size of the separation material or the porous polymer particles of the present embodiment can be determined by the following measurement method.

1) Particles are dispersed in water (including a dispersant such as a surfactant) by using an ultrasonic dispersing apparatus, and a dispersion liquid including 1% by mass of the particles is prepared.

2) The average particle size and the C.V. (coefficient of variation) of the particle size are measured from the images of about 10,000 particles in the dispersion liquid, by using a particle size distribution meter (SYSMEX FLOW FPIA-3000, manufactured by Sysmex Corp.).

The pore size (mode diameter), specific surface area, and the like of the separation material can be adjusted by appropriately selecting the ingredients of the porous polymer particles, the porosifier, the macromolecule having hydroxyl groups, and the like.

The separation material of the present embodiment is suitable for the use in separation of proteins by an electrostatic interaction, affinity purification, and the like. For example, a protein can be collected by the following method, by using a separation material into which an ion exchanging group has been introduced (ion exchanger). When the separation material of the present embodiment is first added to a mixed solution including a protein, only the protein is adsorbed onto the separation material by an electrostatic interaction, and then the separation material is separated by filtration from the solution and added to an aqueous solution having a high salt concentration, the protein that has adsorbed to the separation material can be easily released and collected. Furthermore, the separation material of the present embodiment can also be used as, for example, a separation material for liquid chromatography in column chromatography. The column of the present embodiment comprises the separation material of the present embodiment, and is obtained by, for example, packing the separation material of the present embodiment. An embodiment of a separatory column is illustrated in FIG. 1. A separatory column 10 comprises a column 1; and a separation material 2 packed in the column 1.

As a bio-macromolecule that can be separated by using the separation material of the present embodiment, a water-soluble substance is preferred. Specific examples of bio-macromolecule include proteins, such as blood proteins such as serum albumin (BSA; Bovine Serum Albumin) and immunoglobulin; enzymes existing in the living body; protein physiologically active substances produced by biotechnologies; DNA; and peptides that are physiologically active. The molecular weight of the bio-macromolecule is preferably 2,000,000 or less, and more preferably 500,000 or less. Furthermore, the properties and conditions of the separation material, and the like can be selected, according to known methods, based on the isoelectric point, ionization state and the like of the protein. As the known methods, for example, the method described in JP S60-169427 A and the like may be mentioned.

When porous polymer particles are coated with a crosslinked product of a macromolecule having hydroxyl groups, and then an ion exchanging group, Protein A or the like can be introduced into the particle surface and/or into the pores, the separation material is likely to exhibit the characteristics collectively including the respective advantages possessed by particles formed from natural macromolecules and polymers, in the separation of a bio-macromolecule such as a protein. This performance has not been exhibited in the prior art technologies. Particularly, since the porous polymer particles that serve as the skeleton of the separation material of the present embodiment as such are particles obtainable by a method such as described above, the porous polymer particles have excellent durability and alkali resistance. Furthermore, by coating a crosslinked product of the macromolecule having hydroxyl groups, it is even more difficult for non-specific adsorption to occur, and desorption and adsorption of proteins tend to occur easily. Moreover, the separation material of the present embodiment has preferable properties compared to conventional ion exchange resins, also from the viewpoint that the separation material has a large adsorption capacity (dynamic adsorption capacity) for a protein or the like at the same flow rate.

The "liquid permeation rate" according to the present embodiment represents the liquid permeation rate when a stainless steel column having a size of ϕ7.8×300 mm is packed with the separation material of the present embodiment, and a liquid is caused to flow therethrough. In a case in which the separation material of the present embodiment is packed into the column, it is preferable that the liquid permeation rate (flow rate) when the column pressure is 0.3 MPa is 800 cm/h or higher, more preferably 1,000 cm/h or higher, even more preferably 1,300 cm/h or higher, and particularly preferably 1,500 cm/h or higher. In a case in which separation of a protein is performed by column chromatography, the liquid permeation rate of a protein solution or the like that is passed through the column is generally in the range of 400 cm/h or less. However, in a case in which the separation material of the present embodiment is used, the separation material can be used with a high adsorption capacity even at 800 cm/h or higher, which is a liquid permeation rate that is faster than that of a conventional separation material for protein separation.

When the separation material of the present embodiment is used as a column packing material in column chromatography, since there is hardly any volume change in the column independently of the properties of the eluent used, excellent operability is obtained.

In the present embodiment, a separation material in the form of having an ion exchanging group introduced therein has been mainly explained; however, even if an ion exchanging group is not introduced, the separation material can be used as a separation material. Such a separation material can be utilized in, for example, gel permeation chromatography. That is, the separatory column of the present embodiment comprises a column, and the separation material of the present embodiment packed in the column.

Second Embodiment

According to a second embodiment, the compressive deformation ratio at the time when the separation material of the present embodiment in a wet state is compressed at 50 mN, is less than 30% of the particle size. The ratio of the compression recovery rate in a wet state with respect to the compression recovery rate in a dry state (compression recovery rate ratio; wet state/dry state) at the time when the separation material of the present embodiment is compressed at 50 mN is 0.8 or higher. According to the second embodiment, a separation material that has excellent liquid permeability, reduces non-specific adsorption of proteins, and has an excellent protein adsorption amount, as well as a separatory column that uses the separation material can be provided. Here, the "wet state" refers to a state that is saturated with moisture. The "dry state" refers to a state that does not include moisture (for example, a state in which moisture has been eliminated by a vacuum, heating and drying, or the like). In order to maintain a wet state, it is preferable to use the separation material after taking out the separation material from water immediately before the measurement.

The compressive deformation ratio and the compression recovery rate of the separation material of the present embodiment can be measured by, for example, the following method.

The load and compression displacement at the time when a separation material is compressed up to 50 mN by means of a smooth cross-section (50 μm×50 μm) of a quadrangular prism at room temperature (25° C.) at a load loading rate of 1 mN/sec, by using a microcompression testing machine (manufactured by Fisher Scientific Co., LLC). The compressive deformation ratio can be calculated by the following formula (1) from the maximum amount of displacement at that time.

Compressive deformation ratio (%)=(Amount of deformation in the particle size at the time of 50 mN compression)/average particle size×100   (1)

The compressive deformation ratio of the separation material in a wet state is less than 30%, from the viewpoint of having excellent liquid permeability, reducing non-specific adsorption of proteins, and having an excellent protein adsorption amount. In a case in which the compressive deformation ratio is 30% or higher, since the separation material undergoes excessive deformation, when the separation material is used in a column, the separation material is consolidated in the column, and the column pressure is increased. Furthermore, in a case in which the compressive deformation ratio is 30% or higher, when a liquid is passed through the column, the separation material may be destroyed, and the column may be clogged. The compressive deformation ratio of the separation material in a wet state is preferably 25% or lower, and more preferably 20% or lower, from the viewpoint of having superior liquid permeability, further reducing non-specific adsorption of proteins, and having a superior protein adsorption amount.

The compression recovery rate can be calculated by the following formula (2) from the amount of displacement at the time when unloading is performed from a state of being compressed at 50 mN to 0 mN at a rate of 1 mN/sec.

Compression recovery rate (%)=(Amount of displacement at the time when unloading is carried out from 50 mN to 0 mN)/(amount of deformation of particle size upon compression at 50 mN)   (2)

The compression recovery rate in a wet state is preferably 70% or higher, and more preferably 80% or higher. In a case in which the compression recovery rate is 70% or higher, plastic deformation caused by compression does not easily occur, and therefore, the column pressure is not easily increased.

The compression recovery rates of the separation material in a wet state and in a dry state are measured, and the compression recovery rate ratio can be calculated by the following formula (3):

Compression recovery rate ratio=(Compression recovery rate in wet state)/(compression recovery rate in dry state)   (3)

The compression recovery rate is 0.8 or higher, from the viewpoint of having excellent liquid permeability, reducing non-specific adsorption of proteins, and having an excellent protein adsorption amount. In a case in which the compression recovery rate is less than 0.8, since the separation material becomes flexible by swelling, the column pressure will increase when the separation material is used in a column. From the viewpoint of having superior liquid permeability, further reducing non-specific adsorption of proteins, and having a superior protein adsorption amount, the compression recovery ratio is preferably 0.9 or higher, and more preferably 0.95 or higher.

The separation material according to the second embodiment has excellent liquid permeability when used as a column packing material, reduces non-specific adsorption of proteins, and has an excellent protein adsorption amount. Furthermore, according to the second embodiment, a column packing material that has no non-specific adsorption based on hydrophobic interaction, and separates and purifies a bio-macromolecule by means of electrostatic interaction or affinity purification, while maintaining excellent separation ability for the separation of bio-macromolecules such as proteins, which ability is possessed by a packing material having a hydrophilic natural macromolecule as a matrix, can be provided as a packing material that solves the conventional problems of natural macromolecules and polymer particles.

Third Embodiment

According to a third embodiment, the 5% compressive deformation modulus of the separation material in a wet state is 100 MPa or greater. Furthermore, the ratio of the 5% compressive deformation modulus in a dry state with respect to the 5% compressive deformation modulus in a wet state (5% compressive deformation modulus ratio, dry state/wet state) of the separation material of the present embodiment is 1.85 or higher. According to the third embodiment, a separation material that reduces non-specific adsorption of proteins and has an excellent protein adsorption amount, as well as a separatory column that uses the separation material can be provided. Here, the "wet state" refers to a state that is saturated by moisture. The "dry state" refers to a state that does not include moisture (for example, a state in which moisture has been eliminated by a vacuum, heating and drying, or the like). In order to maintain a wet state, it is preferable to use the separation material after taking out the separation material from water immediately before measurement is made.

The 5% compressive deformation modulus (for example, 5% compressive deformation modulus at the time when the separation material is compressed at 50 mN) of the separation material of the present embodiment can be calculated as follows.

The load and compression displacement at the time when a separation material is compressed from 0 mN to 50 mN by means of a smooth cross-section (50 μm×50 μm) of a quadrangular prism at room temperature (25° C.) at a load loading rate of 1 mN/sec, by using a microcompression testing machine (manufactured by Fisher Scientific Co., LLC). The compressive deformation modulus (5% K value) at the time when a separation material has undergone 5% compressive deformation can be determined by the following formula, from the measurement values thus obtained.

$$5\% \ K \text{ value (MPa)} = (3/2^{1/2}) \times F \times S^{-3/2} \times R^{-1/2}$$

F: Load (mN) at the time when the separation material has undergone 5% compressive deformation S: Compression displacement (m) at the time when the separation material has undergone 5% compressive deformation R: Radius (m) of the separation material The 5% compressive deformation modulus of the separation material in a wet state is 100 MPa or greater. In a case in which the 5% compressive deformation modulus of the separation material in a wet state is less than 100 MPa, flexibility of the separation material is enhanced, and thus, the separation material is easily deformed. Therefore, the separation material is consolidated in the column, and the column pressure rises. As the result, liquid permeability of the column is deteriorated, and the protein adsorption amount tends to decrease. Furthermore, gaps between the coating layer and the porous polymer particles are likely to be generated due to a deformation of the separation material, and as protein adsorbs to the gaps, the non-specific adsorption amount of protein tends to increase. In a case in which the 5% compressive deformation modulus of the separation material in a wet state is 100 MPa or greater, an increase in such a column pressure is suppressed, and deformation of the separation material is suppressed. Thus, non-specific adsorption of proteins is reduced, and an excellent protein adsorption amount is obtained. From the viewpoint of further reducing non-specific adsorption of proteins and obtaining a superior protein adsorption amount, the 5% compressive deformation modulus of the separation material in a wet state is preferably 110 MPa or greater, more preferably 120 MPa or greater, and even more preferably 130 MPa or greater. The 5% compressive deformation modulus of the separation material in a wet state is, for example, 1,000 MPa or less.

The 5% compressive deformation modulus of the separation material in a dry state is preferably 180 MPa or greater, more preferably 250 MPa or greater, and even more preferably 300 MPa or greater, from the viewpoint of preventing disintegration of the particles.

According to the present embodiment, the ratio of the 5% compressive deformation modulus in a state with respect to the 5% compressive deformation modulus in a wet state of the separation material is 1.85 or higher. In a case in which the 5% compressive deformation modulus ratio is less than 1.85, since the surface of the separation material lacks hydrophilicity, non-specific adsorption increases. Furthermore, since the number of hydroxyl groups in the coating layer is small, even in a case in which an ion exchanging group is introduced, the amount of the ion exchanging groups tends to be small Therefore, it is difficult to improve the dynamic adsorption amount.

The 5% compressive deformation modulus ratio can be obtained by measuring the respective 5% compressive deformation modulus of the separation material in a wet state and in a dry state, and calculating the ratio by the following formula.

5% Compressive deformation modulus ratio=(5% Compressive deformation modulus in dry state)/ (5% compressive deformation modulus in wet state)

From the viewpoint of further reducing non-specific adsorption of proteins and having a superior protein adsorption amount, the 5% compressive deformation modulus ratio is preferably 1.9 or higher, more preferably 2.0 or higher, even more preferably 2.2 or higher, and particularly preferably 2.5 or higher. From the viewpoint of further reducing non-specific adsorption of proteins and having a superior protein adsorption amount, the 5% compressive deformation modulus ratio is preferably 3.5 or less, more preferably 3.3 or less, and even more preferably 3.1 or less.

The 5% compressive deformation modulus of the separation material can be adjusted by the type and amount of use of a crosslinking agent, the amount of a coating layer, and the like. For example, as the amount of use of the crosslinking agent or the amount of the coating layer is larger, the 5% compressive deformation modulus tends to increase.

The separation material according to the third embodiment reduces non-specific adsorption of proteins, and has an excellent protein adsorption amount. The separation material according to the third embodiment also has excellent durability. Furthermore, according to the present embodiment, a column packing material that has no non-specific adsorption based on hydrophobic interaction, and separates and purifies a bio-macromolecule by means of electrostatic interaction or affinity purification, while maintaining excellent separation ability for the separation of bio macromolecules such as proteins, which ability is possessed by a packing material having a hydrophilic natural macromolecule as a matrix, can be provided as a packing material that solves the conventional problems of natural macromolecules and polymer particles.

EXAMPLES

Hereinafter, the present invention will be described by way of Examples; however, the present invention is not intended to be limited to these Examples.

Test Example 1

Example 1

<Synthesis of Porous Polymer Particles 1>

16 g of divinylbenzene (manufactured by Nippon Steel & Sumikin Chemical Co., Ltd., trade name: DVB960) having a purity of 96%, 6 g of SPAN 80, and 0.64 g of benzoyl peroxide were introduced into a 500-mL three-necked flask, and an aqueous solution of polyvinyl alcohol (0.5% by mass) was prepared. This aqueous solution was emulsified by using a MICRO PROCESS SERVER, subsequently the emulsion liquid thus obtained was transferred into a flask, and the emulsion liquid was stirred for about 8 hours by using a stirrer, while being heated in a water bath at 80° C. The particles thus obtained were filtered, and then washed with acetone. Thus, porous polymer particles 1 were obtained. The particle size of the porous polymer particles 1 thus obtained was measured with a flow type particle size analyzer, and the average particle size and the C.V. (coefficient of variation) of the particle size were calculated by the method described above. The results are presented in Table 1.

<Formation and Crosslinking of Coating Layer>

4 g of sodium hydroxide and 0.14 g of glycidyl phenyl ether were introduced into 100 mL of an aqueous solution of agarose (2% by mass), and the mixture was reacted for 12 hours at 70° C. Thus, phenyl groups were introduced into agarose. The modified agarose thus obtained was reprecipitated with isopropyl alcohol, and was washed.

The porous polymer particles 1 were introduced into a 20 mg/mL aqueous solution of the modified agarose at a proportion of 1 g of the porous polymer particles 1 in 70 mL of the aqueous solution, and the mixture was stirred for 24 hours at 55° C. Thereby, the modified agarose was adsorbed onto the porous polymer particles 1. After adsorption, the porous polymer particles were filtered and washed with hot water. The adsorption amount of the modified agarose to the particles was calculated by measuring the thermal weight reduction of the particles that had been dried.

The modified agarose was crosslinked as follows. The porous polymer particles 1 with the modified agarose adsorbed thereto were introduced into an aqueous solution in which the concentrations of ethylene glycol diglycidyl ether and sodium hydroxide were 0.64 M and 0.4 M, respectively, at a proportion of 1 g of the particles were introduced into 35 mL of the aqueous solution, and the mixture was stirred for 24 hours at 30° C. Subsequently, the resultant was washed with a heated 2 mass % aqueous solution of sodium dodecyl sulfate, and then washed with pure water. Thus, a separation material was obtained. The separation material thus obtained was dried, and then the mass of the coating layer per 1 g of the porous particles was measured by a thermogravimetric analysis.

(Evaluation of Non-Specific Adsorption Ability for Protein)

0.5 g of the separation material thus obtained was introduced into 50 mL of a phosphate buffer solution (pH 7.4) at a BSA (Bovine Serum Albumin) concentration of 20 mg/mL, and the solution was stirred at room temperature for 24 hours. Subsequently, a supernatant was collected by centrifugation, the BSA concentration of the filtrate was measured with a spectrophotometer, and thus the amount of BSA adsorbed to the separation material was calculated as the non-specific adsorption amount. The concentration of BSA was checked from the absorbance of light at 280 nm by means of a spectrophotometer. The results are presented in Table 2.

<Introduction of Ion Exchanging Group>

The separation material thus obtained was centrifuged so as to remove water, and then the separation material was introduced into a 5 M aqueous solution of sodium hydroxide. The mixture was left to stand for 1 hour at room temperature. The mixture was dispersed in 16 mL of water in which a predetermined amount of diethylaminoethyl chloride hydrochloride had been dissolved, the dispersion was mixed with 128 mL of isopropyl alcohol, and thereby the mixture was added to a composite in a state of being impregnated with sodium hydroxide. Temperature was raised to 70° C., and the mixture was reacted for 5 hours while being stirred. After completion of the reaction, filtering and washing with water was performed, and thus a DEAE-modified separation material having a diethylaminoethyl (DEAE) group as an ion exchanging group was obtained. The average pore size and the specific surface area of the DEAE-modified separation material thus obtained were measured by a mercury intrusion method. The results are presented in Table 2.

The ion exchange capacity of the DEAE-modified separation material thus obtained was measured as follows. The particles in a volume of 5 mL were immersed in 20 mL of 0.1 N sodium hydroxide for 1 hour, and the system was stirred at room temperature. Subsequently, the particles were washed with water so that the pH of the solution would be 7 or lower. The particles thus obtained were immersed in 20 mL of 0.1 N hydrochloric acid, and were stirred for 1 hour. After the particles were filtered, an aqueous solution of hydrochloric acid of the filtrate was titrated to neutralization, and thereby the ion exchange capacity of the DEAE-modified separation material was measured.

(Evaluation of Column Characteristics)

The DEAE-modified separation material thus obtained was packed into a stainless steel column having a size of ϕ7.8×300 mm over 15 minutes as a slurry (solvent: methanol) at a concentration of 30% by mass. Subsequently, water was caused to flow through the column while the flow rate was varied, and the relation between the flow rate and the column pressure was measured. Thus, the liquid permeation rate (linear flow rate) at 0.3 MPa was measured. The results are presented in Table 2.

The dynamic adsorption amount was measured as follows. A 20 mmol/L Tris-hydrochloric acid buffer solution (pH 8.0) was passed through a column in an amount equivalent to 10 column volumes. Subsequently, a 20 mmol/L Tris-hydrochloric acid buffer solution at a BSA concentration of 2 mg/mL was passed through the column, and the BSA concentration at the column outlet was measured by UV measurement. The buffer solution was passed until the BSA concentration at the column inlet coincided with the BSA concentration at the column outlet, and dilution was performed with a 1 M NaCl Tris-hydrochloric acid buffer solution in an amount equivalent to 5 column volumes. The dynamic adsorption amount in 10% breakthrough was calculated by using the following formula. The results are presented in Table 2.

$$q_{10}=c_f F(t_{10}-t_0)/V_B$$

$q_{10}$: dynamic adsorption amount (mg/mL of wet resin) at 10% breakthrough cf: concentration (mg/mL) of BSA that has been injected in F: flow rate (mL/min)

$V_B$: bed volume (mL)

$t_{10}$: time (min) at 10% breakthrough $t_0$: BSA injection initiation time (min)

(Evaluation of Alkali Resistance)

The DEAE-modified separation material thus obtained was stirred in a 0.5 M aqueous solution of sodium hydroxide for 24 hours, and the DEAE-modified separation material was washed with a phosphate buffer solution. Subsequently, the DEAE-modified separation material was packed under the same conditions as for the evaluation of column characteristics. The 10% breakthrough dynamic adsorption amount of BSA was measured, and was compared with the dynamic adsorption amount before an alkali treatment. A case in which the decrease ratio of the dynamic adsorption amount was 3% or less rated as "A"; a case in which the decrease ratio was more than 3% and 20% or less was rated as "B"; and a case in which the decrease ratio was more than 20% was rated as "C". The results are presented in Table 2.

(Degree of Hygroscopicity and 5% Compressive Deformation Modulus)

The degree of hygroscopicity and the 5% compressive deformation modulus were measured by the methods described above. The results are presented in Table 2.

Example 2

Porous polymer particles 2 were synthesized in the same manner as in the synthesis of the porous polymer particles 1, except that the amount of use of SPAN 80 was changed to 8 g. The porous polymer particles 2 thus obtained were treated by a method similar to that for the porous polymer particles 1, and thereby a separation material and a DEAE-modified separation material were obtained. The separation material and the DEAE-modified separation material were subjected to an evaluation similar to that of Example 1.

Example 3

Porous polymer particles 3 were synthesized in the same manner as in the synthesis of the porous polymer particles 1, except that divinylbenzene (16 g) was changed to 12 g of divinylbenzene and 4 g of octanol. The porous polymer particles 3 thus obtained were treated by a method similar to that for the porous polymer particles 1, and thereby a separation material and a DEAE-modified separation material were obtained. The separation material and the DEAE-modified separation material were subjected to an evaluation in the same manner as in Example 1.

Example 4

Porous polymer particles 4 were synthesized in the same manner as in the synthesis of the porous polymer particles 1, except that the amount of use of SPAN 80 was changed to 4 g. The porous polymer particles 4 thus obtained were treated by a method similar to that for the porous polymer particles 1, and thereby a separation material and a DEAE-modified separation material were obtained. The separation material and the DEAE-modified separation material were subjected to an evaluation in the same manner as in Example 1.

Example 5

Porous polymer particles 5 were synthesized in the same manner as in the synthesis of the porous polymer particles 1, except that the amount of use of SPAN 80 was changed to 3 g. The porous polymer particles 5 thus obtained were treated by a method similar to that for the porous polymer particles 1, and thereby a separation material and a DEAE-modified separation material were obtained. The separation material and the DEAE-modified separation material were subjected to an evaluation in the same manner as in Example 1.

Comparative Example 1

Porous polymer particles 6 were synthesized in the same manner as in the synthesis of the porous polymer particles 1, except that divinylbenzene (16 g) and SPAN 80 (6 g) were changed to divinylbenzene (4 g), dihydroxypropyl methacrylate (8 g), and SPAN 80 (4 g). The porous polymer particles 6 thus obtained were modified with DEAE without performing the formation and crosslinking of a coating layer based on a macromolecule having hydroxyl groups (agarose), and thus a separation material was obtained. The separation material was subjected to an evaluation in the same manner as in Example 1.

Comparative Example 2

Commercially available agarose particles (CAPTO DEAE; GE Healthcare Co.) were used as porous polymer particles 7. Furthermore, the porous polymer particles 7 were used as a separation material without any modification. The separation material was subjected to an evaluation in the same manner as in Example 1.

Comparative Example 3

Porous polymer particles 8 were synthesized in the same manner as in the synthesis of the porous polymer particles 1, except that divinylbenzene (16 g) and SPAN 80 (6 g) were changed to 2,3-dihydroxypropyl methacrylate (11.2 g), ethylene glycol dimethacrylate (4.8 g), and SPAN 80 (5 g). The porous polymer particles 8 (4 g) after washing were added to 6 g of a solution obtained by dissolving 1 g of dextran (molecular weight: 150,000), 0.6 g of sodium hydroxide, and 0.15 g of sodium borohydride in distilled water, and the solution was impregnated into the pores of the porous polymer particles 8. The dextran solution-impregnated polymer thus obtained was added to 1 L of a 1 mass % ethyl cellulose-toluene solution with stirring, and the polymer was dispersed and suspended. 5 mL of epichlorohydrin was added to the suspension liquid thus obtained, and the temperature was increased to 50° C. The mixture was stirred for 6 hours at this temperature, and thereby the dextran impregnated in the pores of the porous polymer particles 8 was subjected to a crosslinking reaction. After completion of the reaction, the suspension liquid was filtered to separate a gel-like substance thus produced, and this gel-like substance was washed sequentially with toluene, ethanol, and distilled water. Thus, a separation material was obtained. The separation material was evaluated in the same manner as in Example 1.

Comparative Example 4

Porous polymer particles 9 were synthesized in the same manner as in the synthesis of the porous polymer particles 1, except that divinylbenzene (16 g) was changed to 4 g of divinylbenzene (manufactured by Nippon Steel & Sumitomo Metal Corp., trade name: DVB960) and 12 g of styrene. The porous polymer particles 9 thus obtained were treated by a method similar to that for the porous polymer particles 1, and thereby a separation material was obtained. The separation material was evaluated in the same manner as in Example 1.

Test Example 2

Example 6

(Synthesis of Porous Polymer Particles 10)

In a 500-mL three-necked flask, 16 g of divinylbenzene (DVB960, manufactured by Nippon Steel & Sumikin Chemical Co., Ltd.) having a purity of 96% by mass as a monomer, 16 g of hexanol and 16 g of toluene as porosifiers, and 0.64 g of benzoyl peroxide as an initiator were added to an aqueous solution of polyvinyl alcohol (0.5% by mass) as a dispersion stabilizer. Next, this aqueous solution of polyvinyl alcohol was emulsified by using a MICRO PROCESS SERVER. The emulsion liquid thus obtained was transferred into a flask, and was stirred for about 8 hours by using a stirrer while being heated in a water bath at 80° C. The particles thus obtained were filtered and then were washed with acetone. Thus, porous polymer particles 10 were obtained. The average particle size of the porous polymer particles 10 thus obtained was measured with a flow type particle size analyzer (FPIA-3000, manufactured by Sysmex Corp.), and the average particle size and the C.V. value of the particle size were calculated (Table 3).

(Formation of Coating Layer: Coating by Water-Soluble Macromolecule Having Hydroxyl Groups)

4 g of sodium hydroxide and 0.14 g of glycidyl phenyl ether were added to 100 mL of an aqueous solution of agarose (2% by mass), and the mixture was reacted for 12 hours at 70° C. Thus, a phenyl group was introduced into agarose. The modified agarose thus obtained was precipitated with isopropyl alcohol and washed.

The modified agarose thus obtained was dissolved again in water, and thus a 20 mg/mL aqueous solution of the modified agarose was prepared. Into 70 mL of this aqueous solution of the modified agarose, the porous polymer particles 10 were introduced at a proportion of 1 g, and the mixture was stirred for 24 hours at 55° C. Thus, the modified agarose was adsorbed onto the porous polymer particles 10, and a coating layer was formed on the surface of the porous polymer particles 10. Subsequently, filtering was performed, and the porous polymer particles were washed with hot water.

The agarose that had adsorbed onto the particle surface and the interior of the pores was crosslinked as follows. The particles were introduced into an aqueous solution including ethylene glycol diglycidyl ether at 0.64 M and sodium hydroxide at 0.4 M, at a proportion of 1 g of the particles in 35 mL of the aqueous solution, and the mixture was stirred for 24 hours at room temperature. Subsequently, the par-

TABLE 1

| Item | Average particle size (μm) | Particle size C.V. (%) |
|---|---|---|
| Porous polymer particles 1 | 91 | 12 |
| Porous polymer particles 2 | 93 | 8 |
| Porous polymer particles 3 | 95 | 7 |
| Porous polymer particles 4 | 89 | 10 |
| Porous polymer particles 5 | 91 | 11 |
| Porous polymer particles 6 | 92 | 34 |
| Porous polymer particles 7 | 98 | 38 |
| Porous polymer particles 8 | 92 | 45 |
| Porous polymer particles 9 | 95 | 11 |

TABLE 2

| Item | Mode diameter in pore size distribution (μm) | 5% Compressive deformation modulus (MPa) | Coating amount (mg/g of porous polymer particles) | Specific surface area (m$^2$/g) | Ion exchange capacity (mmol/ml) | Linear flow rate (cm/h) at 0.3 MPa | Non-specific adsorption (mg/mL of particles) | Dynamic adsorption amount (mg/mL of particles) | Alkali resistance | Degree of hygroscopicity (%) |
|---|---|---|---|---|---|---|---|---|---|---|
| Example 1 | 0.3 | 512 | 209 | 52.3 | 0.45 | 1700 | 1 mg or less | 53 | A | 10 |
| Example 2 | 0.5 | 254 | 160 | 40.1 | 0.37 | 1530 | 1 mg or less | 58 | A | 5 |
| Example 3 | 0.5 | 123 | 200 | 50.1 | 0.41 | 1230 | 1 mg or less | 42 | A | 4 |
| Example 4 | 0.2 | 759 | 232 | 82.3 | 0.51 | 1100 | 1 mg or less | 40 | A | 15 |
| Example 5 | 0.15 | 950 | 289 | 95.1 | 0.63 | 1050 | 1 mg or less | 36 | A | 18 |
| Comparative Example 1 | 0.1 | 57 | — | 93.2 | 0.12 | 540 | 5 mg | 15 | B | 52 |
| Comparative Example 2 | 0.15 | 52 | — | 82.2 | 0.31 | 700 | 1 mg or less | 20 | A | 140 |
| Comparative Example 3 | 0.1 | 87 | — | 15.4 | 0.23 | 420 | 3 mg | 12 | B | 51 |
| Comparative Example 4 | 1.4 | 64 | 40 | 10.1 | 0.12 | 630 | 1 mg or less | 16 | A | 3 | ticles were washed with a heated 2 mass % aqueous solution of sodium dodecyl sulfate, and then were washed with pure water. Thus, a separation material was obtained.

The separation material (dry mass 20 g) obtained by filtering an aqueous suspension including the separation material was introduced into 200 mL of a 5 M aqueous solution of sodium hydroxide, and the separation material was left to stand for 1 hour at room temperature. Separately, water was added to a predetermined amount (60 g) of diethylaminoethyl chloride hydrochloride, and the mass was adjusted to 200 g. After the aqueous solution was added, the temperature was raised to 70° C., and the aqueous solution was reacted for 2 hours while being stirred. After completion of the reaction, the product was separated by filtration, and a DEAE-modified separation material having a diethylaminoethyl (DEAE) group as an ion exchanging group was obtained.

The pore volume (porosity), pore size (mode diameter), and specific surface area of the DEAE-modified separation material thus obtained were measured by a mercury intrusion method. The separation material was compressed up to 50 mN by means of a smooth cross-section (50 μm×50 μm) of a quadrangular prism at room temperature (25° C.) at a load loading rate of 1 mN/sec by using a microcompression testing machine (manufactured by Fisher Scientific Co., LLC), and the compressive deformation ratio, the compression recovery rates in a wet state and in a dry state, and the compression recovery rate ratio of the DEAE-modified separation material were measured. The results are presented in Table 4.

The DEAE-modified separation material was dried, and then the amount of the coated water-soluble macromolecule having hydroxyl groups was quantitatively determined by a thermogravimetric analysis. Specifically, the weight reduction of the modified agarose and the porous polymer particles was measured by a thermogravimetric analysis, and the amount of the modified agarose per 1 g of the porous polymer particles was calculated.

(Evaluation of Column Characteristics)

The DEAE-modified separation material was packed into a stainless steel column having a size of ϕ7.8×300 mm as a slurry (solvent: methanol) at a concentration of 30% by mass over 15 minutes. Subsequently, water was caused to flow through the column while the flow rate was varied, and the relation between the flow rate and the column pressure was measured. Thus, the linear flow rate (column flow rate) at a column pressure of 0.3 MPa was measured. The results are presented in Table 5.

Furthermore, the dynamic adsorption amount was measured as follows. A 20 mmol/L Tris-hydrochloric acid buffer solution (pH 8.0) was caused flow through the column in an amount of 10 column volumes. Subsequently, a 20 mmol/L Tris-hydrochloric acid buffer solution having a BSA concentration of 2 mg/mL was caused to flow at 800 cm/h, and the BSA concentration at the column outlet was measured by means of UV. The buffer solution was caused to flow until the BSA concentration at the column inlet coincided with the BSA concentration at the column outlet, and dilution was performed with 5 column volumes of a Tris-hydrochloric acid buffer solution of 1 M NaCl. The dynamic adsorption amount (dynamic binding capacity) at 10% breakthrough was calculated by using the following formula.

$$q_{10}=c_f F(t_{10}-t_0)/V_B$$

$q_{10}$: dynamic adsorption amount (mg/mL of wet resin) at 10% breakthrough $c_f$: concentration (mg/mL) of BSA that has been injected in F: flow rate (mL/min)

$V_B$: bed volume (mL)

$t_{10}$: time (min) at 10% breakthrough $t_0$: BSA injection initiation time (min)

When the dynamic adsorption amount was 50 mg/mL of particles or more, the case was evaluated as "A"; when the dynamic adsorption amount was more than 20 mg/mL of particles and less than 50 mg/mL of particles, the case was rated as "B"; and when the dynamic adsorption amount was 20 mg/mL of particles or less, the case was evaluated as "C". The results are presented in Table 5. Meanwhile, the unit "mg/mL of particles" represents the adsorption amount expressed in the unit mg per 1 mL of the particle volume.

The separation ability for proteins was measured as follows. 15.2 mg of transferrin (TRA) and 26.4 mg of bovine serum albumin (BSA) were weighed. To these, a 0.05 M Tris eluent (pH 8) was added until the total mass became 1 g, and thus a Tris solution A including TRA and BSA at proportions of 1.52% by mass and 2.63% by mass, respectively, was prepared. A column packed with the DEAE-modified separation material obtained as described above was connected to a GPC analyzer, and as an initiating eluent, a 0.05 M Tris eluent (pH 8) was transported for 15 minutes at a flow rate of 1 mL/min Subsequently, 20 μL of the Tris solution A thus prepared was introduced with a microsyringe. Subsequently, a 0.05 M Tris eluent (pH 8) was transported for 10 minutes, and then salt concentration gradient elution was performed by using a 1 M NaCl solution. The light absorbance of the eluate was measured, and the degree of separation was calculated by using the following formula.

$$R=1.18\times(T_{R2}-T_{R1})/(W_{(1/2)1}+W_{(1/2)2})$$

R: degree of separation $T_{R1}$, $T_{R2}$: retention times for two components ($T_{R1}<T_{R2}$)

$W_{(1/2)1}$, $W_{(1/2)2}$: half value widths of the respective peaks

When the degree of separation R was 1.15 or more, the case was rated as "S"; when the degree of separation R was larger than 1 and less than 1.15, the case was rated as "A"; and the degree of separation R was 1 or less, the case was evaluated as "B". The results are presented in Table 5.

Example 7

Porous polymer particles 11 were synthesized by a method similar to that for the synthesis of the porous polymer particles 10, except that 18 g of hexanol and 14 g of toluene were used as porosifiers, and the average particle size and the particle size C.V. were measured. Furthermore, production and evaluation of a DEAE-modified separation material was carried out in the same manner as in Example 6, except that the porous polymer particles 11 were used, and this was designated as Example 7. The results are presented in Tables 3 to 5.

Example 8

Porous polymer particles 12 were synthesized by a method similar to that for the synthesis of the porous polymer particles 10, except that 20 g of hexanol and 15 g of toluene were used as porosifiers, and the average particle size and the particle size C.V. were measured. Furthermore, production and evaluation of a DEAE-modified separation material was carried out in the same manner as in Example 6, except that the porous polymer particles 12 were used, and this was designated as Example 8. The results are presented in Tables 3 to 5.

Example 9

Porous polymer particles 13 were synthesized by a method similar to that for the synthesis of the porous polymer particles 10, except that 25 g of hexanol and 10 g of toluene were used as porosifiers, and the average particle size and the particle size C.V. were measured. Furthermore, production and evaluation of a DEAE-modified separation material was carried out in the same manner as in Example 6, except that the porous polymer particles 13 were used, and this was designated as Example 9. The results are presented in Tables 3 to 5.

Example 10

Porous polymer particles 14 were synthesized by a method similar to that for the synthesis of the porous polymer particles 10, except that the MICRO PROCESS SERVER emulsification conditions were changed, and the particle size was adjusted. The average particle size and the particle size C.V. were measured. Furthermore, production and evaluation of a DEAE-modified separation material was carried out in the same manner as in Example 6, except that the porous polymer particles 14 were used, and this was designated as Example 10. The results are presented in Tables 3 to 5.

Comparative Example 5

Porous polymer particles 15 were synthesized by a method similar to that for the synthesis of the porous polymer particles 10, except that 4 g of divinylbenzene and 12 g of glycidyl methacrylate were used as monomers, and the average particle size and the particle size C.V. were measured. The porous polymer particles 15 thus obtained was washed with water and acetone. After drying, 5 g of the porous polymer particles 15 were immersed for 24 hours in a 50 vol % aqueous solution of diethylamine at 30° C., and thus glycidyl groups were subjected to DEAE-modification. Subsequently, the DEAE-modified porous polymer particles 15 were immersed for 24 hours in a 50 vol % ethanolamine/methanol solution at 30° C., and residual glycidyl groups were blocked. The particles thus obtained were washed and then were evaluated in the same manner as in Example 6, and this was designated as Comparative Example 5. The results are presented in Tables 3 to 5.

Comparative Example 6

Commercially available agarose particles (CaptoDEAE, manufactured by GE Healthcare Co.) were used as porous polymer particles 16 and were evaluated in the same manner as in Example 6, and this was designated as Comparative Example 6.

Comparative Example 7

The porous polymer particles 15 were introduced into 2 mL of an aqueous solution of dextran at a concentration of 160 mg/mL at a proportion of 1 g, and the mixture was stirred for 15 hours at 25° C. Thus, the porous polymer particles 15 were impregnated with dextran. Filtering was performed, and then the porous polymer particles 15 impregnated with dextran were added to 1 L of a 1 mass % ethyl cellulose-toluene solution, and the mixture was dispersed and suspended by stirring. 5 mL of epichlorohydrin was added to the suspension liquid thus obtained, and the temperature was increased to 50° C. The suspension liquid was stirred for 6 hours at this temperature, and thereby the dextran impregnated in the pores of the porous polymer particles 15 was subjected to a crosslinking reaction. After completion of the reaction, the suspension liquid was filtered to separate a gel-like substance thus produced, and the gel-like substance was washed sequentially with toluene, ethanol, and distilled water. Thereby, a separation material was obtained. The separation material was evaluated in the same manner as in Example 6. The results are presented in Tables 4 and 5.

TABLE 3

| Item | Average particle size (μm) | Particle size C.V. (%) |
|---|---|---|
| Porous polymer particles 10 | 91 | 10.2 |
| Porous polymer particles 11 | 93 | 9.8 |
| Porous polymer particles 12 | 95 | 10.1 |
| Porous polymer particles 13 | 89 | 9.7 |
| Porous polymer particles 14 | 63 | 12.3 |
| Porous polymer particles 15 | 94 | 13.1 |
| Porous polymer particles 16 | 94 | 13.2 |

TABLE 4

| | Compression recovery rate ratio (recovery rates of wet state/dry state) | Compressive deformation ratio (%) | Pore volume (volume %) | Mode diameter in pore size distribution (μm) | Specific surface area (m²/g) | Coating amount of water-soluble polymer (mg/g of particles) |
|---|---|---|---|---|---|---|
| Example 6 | 1.01 (88%/87%) | 15 | 58 | 0.13 | 82 | 392 |
| Example 7 | 0.98 (80%/82%) | 20 | 62 | 0.25 | 63 | 301 |
| Example 8 | 1.03 (77%/75%) | 26 | 68 | 0.33 | 52 | 249 |
| Example 9 | 1.01 (71%/70%) | 29 | 51 | 0.51 | 34 | 163 |
| Example 10 | 0.89 (83%/93%) | 28 | 52 | 0.11 | 72 | 344 |
| Comparative Example 5 | 0.73 (33%/45%) | 54 | 56 | 0.12 | 63 | — |
| Comparative Example 6 | 1.03 (77%/75%) | 46 | 62 | 0.09 | 62 | — |
| Comparative Example 7 | 0.62 (33%/53%) | 53 | 45 | 0.08 | 32 | 355 |

TABLE 5

|  | Column flow rate (cm/h) at 0.3 MPa | Protein separation ability | Dynamic adsorption amount (mg/mL of particles) |
|---|---|---|---|
| Example 6 | 1820 | S | A |
| Example 7 | 1730 | S | A |
| Example 8 | 1680 | S | A |
| Example 9 | 1510 | S | A |
| Example 10 | 1580 | S | A |
| Comparative Example 5 | 530 | B | C |
| Comparative Example 6 | 730 | A | B |
| Comparative Example 7 | 370 | A | B |

Test Example 3

Example 11

(Synthesis of porous polymer particles 17)

In a 500-mL three-necked flask, 16 g of divinylbenzene (DVB960, Nippon Steel & Sumikin Chemical Co., Ltd.) having a purity of 96% by mass as a monomer, 16 g of hexanol and 16 g of diethylbenzene as porosifiers, and 0.64 g of benzoyl peroxide as an initiator were added to an aqueous solution of polyvinyl alcohol (0.5% by mass) as a dispersion stabilizer. Next, this aqueous solution of polyvinyl alcohol was emulsified by using a MICRO PROCESS SERVER. The emulsion liquid thus obtained was transferred into a flask, and the emulsion liquid was stirred for about 8 hours by using a stirrer while being heated in a water bath at 80° C. The particles thus obtained were filtered and then were washed with acetone, and thus porous polymer particles were obtained. The average particle size of the porous polymer particles thus obtained was measured with a flow type particle size analyzer (FPIA-3000, manufactured by Sysmex Corp.), and the average particle size and the C.V. value of the particle size were calculated. The average particle size was 89 µm, and the C.V. value of the particle size was 10%. Furthermore, the porosity, pore size (mode diameter), and specific surface area of the porous polymer particles thus obtained were measured by a mercury intrusion method. The results are presented in Table 6.

(Formation of Coating Layer: Coating by Water-Soluble Macromolecule Having Hydroxyl Groups)

4 g of sodium hydroxide and 0.14 g of glycidyl phenyl ether were added to 100 mL of an aqueous solution of agarose (2% by mass), and the mixture was reacted for 12 hours at 70° C. Thus, a phenyl group was introduced into agraose. The modified agarose thus obtained was precipitated with isopropyl alcohol and was washed.

The modified agarose thus obtained was dissolved again in water, and a 20 mg/mL aqueous solution of the modified agarose was prepared. Into 70 mL of this aqueous solution of the modified agarose, the porous polymer particles were introduced at a proportion of 1 g, the mixture was stirred for 24 hours at 55° C., and thereby the modified agarose was adsorbed onto the porous polymer particles. Thus, a coating layer was formed on the surface of the porous polymer particles. Subsequently, filtering was performed, and the particles were washed with hot water. The adsorption amount of agarose onto the porous polymer particles was calculated from the concentration of the modified agarose in the filtrate. The results are presented in Table 7.

(Crosslinking of Adsorbed Macromolecule Having Hydroxyl Groups)

The agarose that had adsorbed onto the particle surface and the interior of the pores was crosslinked as follows. The particles were introduced into an aqueous solution including ethylene glycol diglycidyl ether at 0.64 M and sodium hydroxide at 0.4 M, at a proportion of 1 g of the particles in 35 mL of the aqueous solution, and the mixture was stirred for 10 hours at room temperature. Subsequently, the particles were washed with a heated 2 mass % aqueous solution of sodium dodecyl sulfate, and then were washed with water. Thus, a separation material was obtained.

(Introduction of Amino Group)

A dispersion liquid (aqueous suspension liquid) including the separation material was subjected to centrifugation, and thus water was removed. The separation material thus obtained (dry mass 20 g) was dispersed in 100 mL of an aqueous solution prepared by dissolving a predetermined amount (30 g) of diethylaminoethyl chloride hydrochloride, and the dispersion was stirred for 10 minutes at 70° C. Subsequently, 100 mL of a 5 M aqueous solution of NaOH that had been heated to 70° C. was added to the aqueous solution in which the separation material was dispersed, and the mixture was reacted for 1 hour while being stirred. After completion of the reaction, the product was separated by filtration and was washed two times with water/ethanol (volume ratio 8/2), and thus, a DEAE-modified separation material having a diethylaminoethyl (DEAE) group as an ion exchanging group was obtained.

(Measurement of Pore Volume, Pore Size (Mode Diameter), and Specific Surface Area)

The pore volume (porosity), particle size, and specific surface area of the DEAE-modified separation material were measured by a mercury intrusion method. The results are presented in Table 7.

(Measurement of Ion Exchange Capacity)

The ion exchange capacity of the DEAE-modified separation material was measured as follows. The DEAE-modified separation material in a volume of 5 mL was immersed in 20 mL of a 0.1 N aqueous solution of sodium hydroxide for 1 hour, and the mixture was stirred at room temperature. Subsequently, the mixture was washed with water such that the pH of the solution would be 7 or lower. The particles thus obtained were immersed in 20 mL of 0.1 N hydrochloric acid, and the mixture was stirred for 1 hour. The particles were filtered, subsequently an aqueous solution of hydrochloric acid of the filtrate was titrated to neutralization, and thereby the exchange capacity of the particles was measured. The results are presented in Table 7.

(Measurement of Compressive Deformation Modulus)

DEAE-modified separation material samples in a wet state and in a dry state were compressed from 0 mN to 50 mN by means of a smooth cross-section of a quadrangular prism (50 µm×50 µm) at a load loading rate of 1 mN/sec at room temperature (25° C.), by using a microcompression testing machine (manufactured by Fisher Scientific Co., LLC), and the 5% compressive deformation modulus and the 5% compressive deformation modulus ratio of the DEAE-modified separation material were measured. The results are presented in Table 8.

(Evaluation of Column Characteristics)

The DEAE-modified separation material was packed into a stainless steel column having a size of ϕ7.8×300 mm as a slurry (solvent: methanol) at a concentration of 30% by mass over 15 minutes. Subsequently, water was caused to flow through the column while the flow rate was varied, and the relation between the flow rate and the column pressure was measured. The linear flow rate (column flow rate) at a column pressure of 0.3 MPa was measured. The results are presented in Table 7.

Furthermore, the dynamic adsorption amount of a protein was measured as follows. A 20 mmol/L Tris-hydrochloric acid buffer solution (pH 8.0) was caused to flow through the column in an amount of 10 column volumes. Subsequently, a 20 mmol/L Tris-hydrochloric acid buffer solution having a BSA concentration of 2 mg/mL was caused to flow at 800 cm/h, and the BSA concentration at the column outlet was measured by means of UV. The buffer solution was caused to flow until the BSA concentration at the column inlet coincided with the BSA concentration at the outlet, and dilution was performed with a Tris-hydrochloric acid buffer solution at 1 M NaCl in an amount of 5 column volumes. The dynamic adsorption amount (dynamic binding capacity) at 10% breakthrough was calculated by using the following formula.

$$q_{10} = c_f F(t_{10} - t_0)/V_B$$

$q_{10}$: dynamic adsorption amount (mg/mL of wet resin) at 10% breakthrough $c_f$: concentration (mg/mL) of BSA that has been injected in F: flow rate (mL/min)

$V_B$: bed volume (mL)

$t_{10}$: time (min) at 10% breakthrough $t_0$: BSA injection initiation time (min)

When the dynamic adsorption amount was 50 mg/mL of particles or more, the case was rated as "A"; when the dynamic adsorption amount was less than 50 mg/mL of particles and more than 20 mg/mL of particles, the case was rated as "B"; and when the dynamic adsorption amount was 20 mg/mL of particles or less, the case was rated as "C". The results are presented in Table 9. Meanwhile, the unit "mg/mL of particles" means the dynamic adsorption amount (mg) of a protein per 1 mL of the packed separation material.

(Evaluation of Non-Specific Adsorption Amount of Protein)

0.2 g of the DEAE-modified separation material was introduced into 20 mL of a Tris-hydrochloric acid buffer solution (pH 8.0) having a BSA concentration of 24 mg/mL, and stirring was performed for 24 hours at room temperature. Subsequently, the supernatant was collected by centrifugation, and then the BSA concentration of the filtrate was measured with a spectrophotometer. The amount of BSA adsorbed to the separation material was calculated from this measurement value. The concentration of BSA was checked from the absorbance of light at 280 nm by means of a spectrophotometer. When the non-specific adsorption amount was 1 mg/mL of particles or less, the case was rated as "A"; when the non-specific adsorption amount was more than 1 mg/mL of particles and less than 10 mg/mL of particles, the case was rated as "B"; and when the non-specific adsorption amount was 10 mg/mL of particles or more, the case was rated as "C". The results are presented in Table 9.

(Evaluation of Alkali Resistance)

The DEAE-modified separation material was stirred in a 0.5 M aqueous solution of sodium hydroxide for 24 hours, and was washed with a Tris-hydrochloric acid buffer solution. Subsequently, the DEAE-modified separation material was packed into a column under the same conditions as those for the evaluation of column characteristics. The 10% breakthrough dynamic adsorption amount of BSA was measured, and this was compared with the dynamic adsorption amount before the alkali treatment. When the decrease in the dynamic adsorption amount was 3% or less, the case was rated as "A"; when the decrease in the dynamic adsorption amount was more than 3% and less than 20%, the case was rated as "B"; and when the decrease in the dynamic adsorption amount was 20% or more, the case was rated as "C". The results are presented in Table 9.

(Evaluation of Durability)

A column was packed under the same conditions as those for the evaluation of column characteristics. Water was caused to flow through the column at a flow rate of 800 cm/h, and the column pressure was measured. Subsequently, the flow rate was increased to 3,000 cm/h, and liquid was passed for 1 hour. When the column pressure was decreased to 800 cm/h again, the case in which the column pressure increased by 10% or more compared to the initial value (before the flow rate was increased to 3,000 cm/h) was rated as "B"; and the case in which the increment of the column pressure was less than 10% was rated as "A". The results are presented in Table 9.

Example 12

Production and evaluation of a DEAE-modified separation material was carried out in the same manner as in Example 11, except that the concentration of ethylene glycol diglycidyl ether in the crosslinking of agarose was changed to 0.32 M.

Example 13

Production and evaluation of a DEAE-modified separation material was carried out in the same manner as in Example 11, except that the concentration of ethylene glycol diglycidyl ether in the crosslinking of agarose was changed to 1.28 M.

Comparative Example 8

Production and evaluation of a DEAE-modified separation material was carried out in the same manner as in Example 11, except that the concentration of the aqueous solution of agarose in the formation of the coating layer was changed to 0.5% by mass.

Comparative Example 9

Production and evaluation of a DEAE-modified separation material was carried out in the same manner as in Example 11, except that the concentration of ethylene glycol diglycidyl ether in the crosslinking of agarose was changed to 6.4 M.

TABLE 6

| Item | Average particle size (μm) | Particle size C.V. (%) | Pore size (mode diameter) (μm) | Porosity (volume %) | Specific surface area (m²/g) |
|---|---|---|---|---|---|
| Porous polymer particles 17 | 89 | 10 | 0.1 | 63 | 82.3 |

TABLE 7

| Item | Pore size (mode diameter) (μm) | Porosity (volume %) | Specific surface area (m²/g) | Amount of coating layer (mg/g) | Ion exchange capacity (mmol/ml) | Linear flow rate (cm/h) at 0.3 MPa |
|---|---|---|---|---|---|---|
| Example 11 | 0.10 | 55 | 46 | 410 | 0.35 | 1510 |
| Example 12 | 0.10 | 55 | 45 | 405 | 0.50 | 1100 |
| Example 13 | 0.09 | 54 | 45 | 400 | 0.09 | 1670 |
| Comparative Example 8 | 0.09 | 54 | 45 | 40 | 0.02 | 900 |
| Comparative Example 9 | 0.09 | 54 | 44 | 300 | 0.07 | 1700 |

TABLE 8

| | 5% Compressive deformation modulus (MPa) | | 5% Compressive deformation modulus ratio |
|---|---|---|---|
| Item | Dry state | Wet state | [dry state/wet state] |
| Example 11 | 460 | 180 | 2.56 |
| Example 12 | 370 | 120 | 3.08 |
| Example 13 | 550 | 230 | 2.39 |
| Comparative Example 8 | 180 | 160 | 1.12 |
| Comparative Example 9 | 700 | 390 | 1.79 |

TABLE 9

| Item | Non-specific adsorption (mg/mL of particles) | Dynamic adsorption amount (mg/mL of particles) | Alkali resistance | Durability |
|---|---|---|---|---|
| Example 11 | A | A | A | A |
| Example 12 | A | A | A | A |
| Example 13 | B | B | A | A |
| Comparative Example 8 | C | C | A | A |
| Comparative Example 9 | A | C | A | A |

As is understood from the results of Tables 8 and 9, it was found that when the 5% compressive deformation modulus of the separation material in a wet state is 100 MPa or greater, and the 5% compressive deformation modulus ratio is 1.85 or higher, non-specific adsorption can be reduced, and also, the column characteristics of the dynamic adsorption amount are excellent.

REFERENCE SIGNS LIST

1 . . . Column, 2 . . . Separation material, 10 . . . Separatory column.

The invention claimed is:

1. A separation material comprising:
porous polymer particles that comprise a styrene-based monomer as a monomer unit; and a coating layer that comprises a crosslinked modified agarose modified with a hydrophobic group and covers at least a portion of the surface of the porous polymer particles,
wherein the separation material has a 5% compressive deformation modulus of 100 to 1,000 MPa, and has a mode diameter in the pore size distribution of 0.1 to 0.5 μm, and
the separation material comprises 160 to 410 mg of the coating layer per 1 g of the porous polymer particles.

2. The separation material according to claim 1, wherein the degree of hygroscopicity is 1% to 30% by mass.

3. A separation material comprising:
porous polymer particles; and
a coating layer that covers at least a portion of the surface of the porous polymer particles,
wherein the coating layer comprises a-crosslinked modified agarose modified with a hydrophobic group,
the compressive deformation ratio at the time when the separation material in a wet state is compressed at 50 mN is less than 30% of the particle size,
the ratio of the compression recovery rate in a wet state with respect to the compression recovery rate in a dry state at the time when the separation material is compressed at 50 mN is 0.8 or higher, and
the separation material comprises 160 to 410 mg of the coating layer per 1 g of the porous polymer particles.

4. A separation material comprising:
porous polymer particles; and
a coating layer that covers at least a portion of the surface of the porous polymer particles,
wherein the coating layer comprises a-crosslinked modified agarose modified with a hydrophobic group,
the 5% compressive deformation modulus of the separation material in a wet state is 100 MPa or greater, and
the ratio of the 5% compressive deformation modulus in a dry state with respect to the 5% compressive deformation modulus in a wet state of the separation material is 1.85 or higher, and
the separation material comprises 160 to 410 mg of the coating layer per 1 g of the porous polymer particles.

5. The separation material according to claim 3, wherein the mode diameter in the pore size distribution is 0.05 to 0.5 μm.

6. The separation material according to claim 1, wherein the average particle size of the porous polymer particles is 10 to 500 μm.

7. The separation material according to claim 1, wherein the coefficient of variation of the particle size of the porous polymer particles is 3% to 15%.

8. The separation material according to claim 1, wherein the average particle size of the separation material is 10 to 500 μm.

9. The separation material according to claim 1, wherein the pore volume of the separation material is 30% by volume or more.

10. The separation material according to claim 1, wherein the specific surface area of the porous polymer particles is 30 m²/g or more.

11. The separation material according to claim 1, wherein the specific surface area of the separation material is 30 m²/g or more.

12. The separation material according to claim 1, wherein the porous polymer particles comprise divinylbenzene as a monomer unit at a proportion of 50% by mass or more based on the total mass of the monomers.

13. The separation material according to claim 1, wherein the separation material is configured to be packed in a column and, when the column pressure is 0.3 MPa, provide a liquid permeation rate of 800 cm/h or higher.

14. A separatory column comprising a column; and the separation material according to claim 1 that is packed in the column.

15. The separatory column according to claim 14, wherein, when the column pressure is 0.3 MPa, the liquid permeation rate is 800 cm/h or higher.

16. The separation material according to claim 1, wherein the crosslinked modified agarose modified with a hydrophobic group comprises phenyl agarose.

17. The separation material according to claim 3, wherein the crosslinked modified agarose modified with a hydrophobic group comprises phenyl agarose.

18. The separation material according to claim 4, wherein the crosslinked modified agarose modified with a hydrophobic group comprises phenyl agarose.

* * * * *